United States Patent
Josephson et al.

(10) Patent No.: US 8,546,531 B2
(45) Date of Patent: Oct. 1, 2013

(54) METHODS AND REAGENTS FOR PREPARING MULTIFUNCTIONAL PROBES

(75) Inventors: Lee Josephson, Reading, MA (US); Elisabeth Garanger, Bordeaux (FR)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 13/054,364

(22) PCT Filed: Jul. 15, 2009

(86) PCT No.: PCT/US2009/050714
§ 371 (c)(1), (2), (4) Date: Mar. 9, 2011

(87) PCT Pub. No.: WO2010/009246
PCT Pub. Date: Jan. 21, 2010

(65) Prior Publication Data
US 2011/0159566 A1    Jun. 30, 2011

Related U.S. Application Data

(60) Provisional application No. 61/081,303, filed on Jul. 16, 2008.

(51) Int. Cl.
A61K 38/12   (2006.01)
A61K 38/00   (2006.01)
A61K 49/00   (2006.01)
C07K 5/00    (2006.01)
C07K 16/00   (2006.01)
C07K 1/00    (2006.01)
C12N 9/96    (2006.01)

(52) U.S. Cl.
USPC .......... 530/333; 435/7.1; 435/188; 424/9.1; 530/317; 530/324; 530/391.5; 530/402

(58) Field of Classification Search
USPC ............... 435/7.1, 188; 424/9.1; 530/317, 530/324, 333, 345, 391.5
See application file for complete search history.

(56) References Cited

U.S. PATENT DOCUMENTS

2005/0043215 A1* 2/2005 Minko et al. ............. 514/2
2005/0130167 A1  6/2005 Bao et al.
(Continued)

OTHER PUBLICATIONS

Ivkov et a, lApplication of High Amplitude AlternatingMagnetic Fields for Heat Induction of Nanoparticles Localized in Cancer.2005, Clin Cancer Res., 11, 7093s-7103s.*

(Continued)

Primary Examiner — Narayan Bhat
(74) Attorney, Agent, or Firm — Quarles & Brady, LLP

(57) ABSTRACT

Multifunctional probes are synthesized in a single step using peptide scaffold-based multifunctional single-attachment-point reagents. To obtain multifunctional probes using the methods of the invention, a substrate (e.g., a nanoparticle, polymer, antibody, protein, low molecular weight compound, drug, etc.) is reacted with a multifunctional single-attachment-point (MSAP) reagent. The MSAP reagents can include three components: (i) a peptide scaffold, (ii) a single chemically reactive group on the peptide scaffold for reaction of the MSAP with a substrate having a complementary reactive group, and (iii) multiple functional groups on the peptide scaffold. The peptide scaffold can include any number of residues; however, for ease of synthesis and reproducibility in clinical trials, it is preferred to limit the residues in the peptide to 20 or less. The reagent can be prepared to yield a predetermined stoichiometric ratio of the functional groups on the scaffold such that the probe has a fixed stoichiometric ratio of the functional groups.

20 Claims, 13 Drawing Sheets

(56) References Cited

U.S. PATENT DOCUMENTS

| | | | |
|---|---|---|---|
| 2005/0216961 A1* | 9/2005 | Delaney | 800/10 |
| 2006/0039859 A1* | 2/2006 | Sharma et al. | 424/1.49 |
| 2007/0259365 A1 | 11/2007 | Hah et al. | |
| 2007/0289369 A1 | 12/2007 | Wang et al. | |

OTHER PUBLICATIONS

The International Search Report and Written Opinion as mailed on Mar. 16, 2010 for International Application No. PCT/US2009/050714.

Brooks et al., Integrin avB3 Antagonists Promote Tumor Regression by Inducing Apoptosis of Angiogenic Blood Vessels, Cell, 1994, 79:1157-1164.

Cai et al., Nanoplatforms for Targeted Molecular Imaging in Living Subjects, Small, 2007, 3:1840-1854.

Ferrari, Cancer Nanotechnology: Opportunities and Challenges, Nature Reviews Cancer, 2005, 5:161-171.

Gao et al., In Vivo Cancer Targeting and Imaging with Semiconductor Quantum Dots, Nature Biotechnology, 2004, 22:969-976.

Garanger, et al., Simplified Syntheses of Complex Multifunctional Nanomaterials, Chem. Commun., 2008, 39:4792-4794.

Garanger, et al., A Multifunctional Single-Attachment-Point Reagent for Controlled Protein Biotinylation, Bioconjugate Chem., 2009, 20(1):170-173.

Haubner et al., Radiolabeled avB3 Integrin Antagonists: A New Class of Tracers for Tumor Targeting, J Nucl Med, 1999, 40:1061-1071.

Kircher et al., A Dual Fluorochrome Probe for Imaging Proteases, Bioconjugate Chem., 2004, 15:242-248.

Kumar et al., Directionbal Conjugation of Antibodies to Nanoparticles for Synthesis of Multiplexed Optical Contrast Agents with Both Delivery and Targeting Moieties, Nature Protocols, 2008, 3:314-320.

Li, et al. Site-Specific Labeling of Annexin V with F-18 for Apoptosis Imaging, Bioconjugate Chem., 2008, 19:1684-1688.

Medarova et al., In Vivo Imaging of siRNA Delivery and Silencing in Tumors, Nature Medicine, 2007, 13:372-377.

Oliver, Conjugation of Colloidal Gold to Proteins, Methods in Molecular Biology, 1999, 115:331-334.

Pasqualini et al., av Integrins as Receptors for Tumor Targeting by Circulating Ligands, Nature Biotechnology, 1997, 15:542-546.

Rhyner et al., Quantum Dots and Multifunctional Nanoparticles: New Contrast Agents for Tumor Imaging, Nanomedicine, 2006, 1:209-217.

Sancey et al., In Vivo Imaging of Tumour Angiogenesis in Mice with the avB3 Integrin-Targeted Tracer 99mTc-RAFT-RGD, Eur J Nucl Med Mol Imaging, 2007, 34:2037-2047.

Schellenberger et al., Optimal Modification of Annexin V with Fluorescent Dyes, ChemBioChem, 2004, 5(3):271-274.

Schellenberger et al., Surface-Functionalized Nanoparticle Library Yields Probes for Apoptotic Cells, ChemBioChem, 2004, 5:275-279.

Smith et al., The Antiproliferative Cytostatic Effects of a Self-Activating Viridin Prodrug, Mol Cancer Ther, 2009, 8:1666-1675.

Weissleder et al., Cell-Specific Targeting of Nanoparticles by Multivalent Attachment of Small Molecules, Nature Biotechnology, 2005, 23:1418-1423.

Weissleder et al., In Vivo Imaging of Tumors with Protease-Activated Near-Infrared Fluorescent Probes, Nature Biotechnology, 1999, 17:375-378.

PCT International Preliminary Report on Patentability, PCT/US2009/050714, Jan. 27, 2011.

* cited by examiner a) Sequential modification of a substrate (S) with two monofunctional reagents.

b) Reaction of a substrate with a multifunctional, single-attachment-point (MSAP) reagent.

c) Bifunctional MSAP reagent.

d) Trifunctional MSAP reagent.

a) Fmoc/tBu SPPS: Piperidine/DMF (1:4); Fmoc-Xaa-OH, PyBOP, DIEA, DMF;
b) DTPA(CO₂tBu)₄, PyBOP, DIEA, DMF; c) TFA/H₂O/TIS/EDT (88:2:5:5);
d) succinimidyl 6-(N-(7-nitrobenz-2-oxa-1,3-diazol-4-yl)amino)hexanoate, DIEA, DMF; e) N-[γ-maleimidobutyryloxy]succinimide ester, DIEA, DMF.

METHODS AND REAGENTS FOR PREPARING MULTIFUNCTIONAL PROBES

CROSS-REFERENCE TO RELATED APPLICATIONS

This application claims priority from U.S. Patent Application No. 61/081,303 filed Jul. 16, 2008 and priority from PCT International Application No. PCT/US2009/050714 filed Jul. 15, 2009, all of which are incorporated herein by reference for all purposes.

STATEMENT REGARDING FEDERALLY SPONSORED RESEARCH

This invention was made with government support under grant numbers EB004472 and EB 00662 awarded by the National Institutes of Health. The government has certain rights in the invention.

BACKGROUND OF THE INVENTION

1. Field of the Invention

The invention relates to methods and reagents for preparing multifunctional probes, and more particularly to multifunctional probes that are synthesized in a single step using peptide scaffold-based multifunctional single-attachment-point reagents.

2. Description of the Related Art

The design of new nanomaterials with ever higher levels of multifunctional capability, and consequent chemical complexity, is a common challenge to the fields of drug delivery, in vivo molecular imaging, and sensor development (see, e.g., Ferrari, *Nat Rev Cancer* (2005) 5:161-171; Rhyner et al., 110 *Nanomed* (2006) 1: 209-217; and Cai et al., *Small* (2007) 3:1840-1854). Multifunctionality is relatively easy to achieve with nanoparticles or polymers that afford a large number of similar reactive sites. Multifunctional probes can then be obtained by reacting a substrate with two or more monofunctional reagents each with a reactive group sequentially, see FIG. 1a. Examples of sequential modification strategies abound with quantum dots (see, Gao et al., *Nat Biotechnol* (2004) 22:969-976), gold and magnetic iron oxide nanoparticles (see, Weissleder et al., 115 *Nat Biotechnol* (2005) 23:1418-1423; and Kumar et al., *Nat Protoc* (2008) 3:314-320); and polymers like polylysines (see Weissleder et al., Nat *Biotechnol* (1999) 17:375-378).

However, sequential syntheses of multifunctional probes allow the stoichiometric ratios of functional groups to vary since each group is attached independently. As the number of functional groups increases from two to three or more, the problem of non-stoichiometric functional group attachment escalates. When multifunctional probes are considered for clinical use, a frequent rationale for animal experiments, fixed functional group ratios in each preparation becomes a necessity. In addition, the extent of substrate modification with non-light absorbing functional groups (e.g. chelate, biotin, polymer) sometimes cannot be determined by simple analytical procedures. Yet another limitation of multifunctional probe syntheses using multiple reagents occurs when they are considered for substrates possessing a single reactive center, a situation more frequently encountered as substrate size decreases from nanoparticles (>500 kDa) to small macromolecules (5-50 kDa, e.g. small proteins) or low molecular weight molecules (<5 kDa, e.g. drugs, peptides, hormones). Addition of multiple functional groups is also impossible with substrates like annexin V (32 kDa) which, though affording multiple reactive amines, loses activity after modification of a single amine (see, Schellenberger et al., 120 *Chembiochem* (2004) 5:275-279).

Therefore, there is need for methods and reagents for preparing multifunctional probes such that the multifunctional probes can have controlled stoichiometric ratios of functional groups on the probe.

SUMMARY OF THE INVENTION

The invention addresses the foregoing needs by providing methods and reagents for preparing multifunctional materials, referred to as multifunctional probes. To obtain multifunctional probes using the methods of the invention, a substrate (e.g., a nanoparticle, polymer, antibody, protein, low molecular weight compound, drug, etc.) is reacted with a multifunctional single-attachment-point (MSAP) reagent. Thus:

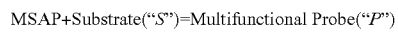

MSAP+Substrate("*S*")=Multifunctional Probe("*P*")

In one form, the MSAPs include multiple functionalities (functional groups, $F^1$, $F^2$, $F^3$) and a single chemically reactive group (RG) attached to a peptide scaffold (PS). Thus, MSAP reagents can include three components: (i) a peptide scaffold (PS), (ii) a single chemically reactive group (RG) for reaction of the MSAP with a substrate having a complementary reactive group, and (iii) multiple functional groups denoted $F^1$, $F^2$, $F^3$, $F^n$. Non-limiting examples of the functional groups include diverse classes of molecules such as fluorochromes, metal chelates, pharmacologically active groups (SiRNA, drugs), immunoreactive haptens, and polymers. Non-limiting examples of the reactive groups include N-hydroxysuccinimide (NHS) ester, maleimide, thiol, alkyne, azide, and aldehyde. Non-limiting examples of the substrates include nanoparticles, proteins, enzymes, cyclic peptides, linear peptides, drugs, and vitamins. In one example form, the substrates include proteins, enzymes, peptides, antibodies, or drugs that can target a specific site (e.g., tumor) in a patient (human or animal) undergoing a diagnostic medical procedure.

In one embodiment, the invention provides a method for the synthesis of multifunctional probes. The method can include the following steps: (1) synthesizing an MSAP reagent, the MSAP being a reagent where more than one functional group and a reactive group are attached to a peptide scaffold; and (2) reacting an MSAP reagent with a substrate to obtain a multifunctional probe.

In another embodiment, the invention provides for certain MSAP reagents as compositions. The general structure of these MSAP reagents can include a peptide scaffold to which at least two functional groups and a single reactive group have been attached. Use of MSAP's simplifies the design of multifunctional probes and improves the quality of those probes.

The MSAP reagents find utility in various applications. The MSAP reagents can be used to visualize the fate of nanomaterials in a biological system using more than one detection modality. They are of particular value when the substrate is a nanoparticle or polymer like polylysine presenting a large number of a single class of reactive groups (e.g. all amines, all carboxyl groups). They also are of value in substrates that lose bioactivity as multiple functional groups are attached; in this class are small proteins like annexin V, single chain antibodies, and some peptides. MSAPs maximize the information that can be obtained from a single substrate while reducing the number of deleterious modifications (FIG. 11). By using an MSAP 0.7 moles of chelator and 0.7 moles of fluorochrome were attached to annexin V. This protein is inactivated when 1.4 moles of amine per mole of protein are modified. See Schellenberger Optimal modification of annexin V with fluorescent dyes. (2004) ChemBiochem 5(3) 271. Several more non-limiting examples of problems addressed by MSAPs follow.

One problem addressed by MSAPs is the fate of radioactive molecules in a biological system detected by microscopy. Radioactive tracers are frequently imaged by positron emission tomography (PET) or single-photon emission computed tomography (SPECT) using whole body imaging equipment. However, it is difficult to ascertain the fate of radioactive tracers in tissues at a cellular or molecular level. Typically, the location of a tracer at this spatial resolution is determined by fluorescence methods, such as by fluorescence microscopy or by dissolving the tissue and quantifying cell-specific fluorescence by fluorescence-activated cell sorting. With MSAPs including a radioactive metal (e.g., $^{99m}$Tc, $^{111}$In, $^{67}$Ga, etc.) chelate ($F^1$) and a fluorochrome ($F^2$), the fate of a biomolecule can be monitored by both radioactivity and fluorescence. This is particularly conceivable since most radioisotopes used in nuclear imaging have short radiochemical half-lifes, so the tissues or organs are soon non-radioactive after whole animal imaging. To address the disposition of MSAPs in biological systems tissues are sectioned and antibodies to MSAP functional groups, like the fluorochrome NBD, are used. The technique is termed fluorochrome immunohistochemistry, see FIG. 4D.

Another problem addressed by MSAPs is the fate of magnetic resonance imaging (MRI) contrast agents in biological systems by microscopy. MRI contrast agents aid in distinguishing between tissue with identical signal characteristics and shorten the relaxation times which produces a stronger signal on T1-weighted spin-echo magnetic resonance images and a less intense signal on T2-weighted images. Examples of MRI contrast agents include gadolinium chelates, manganese chelates, chromium chelates, and iron particles. The fate of metals used as MRI contrast agents (Gd, Mn, Cr, Fe) is difficult to monitor from their chemical properties. Additionally, the change in magnetic resonance contrast they produce does not correlate with their concentration in tissues or biological fluids. MSAPs allow the fate of MRI contrast agents to be monitored by fluorescence microscopy or by whole animal fluorescence tomography.

Yet another problem addressed by MSAPs is the fate of radioactive or MRI contrast agents in biological systems detected by multimodality imaging. By using two imaging modalities, complementary information depicting the fate of an MSAP-conjugated substrate can be determined. For example, a $F^1$-$F^2$-S conjugate, with $F^1$=radioactive metal chelate and $F^2$=near infrared (NIR) fluorochrome or with $F^1$=magnetic resonance active chelate and $F^2$=NIR fluorochrome, enables one to perform non-invasive dual-modality nuclear/optical or magnetic resonance/optical imaging respectively. The MSAPs can work as contrast agents and/or tracers in combinations of various imaging techniques such as PET, SPECT, MRI, computerized tomography (CT), optical imaging (e.g., angiography), and ultrasound.

Still another problem addressed by MSAPs is the facile monitoring of the fate of MSAP intermediates during chemical synthesis. For example the absorbance of NBD was used to monitor the attachment of an MSAP to RGD peptide (see FIG. 4C). A second example is the use of fluorescein's fluorescent to monitor the attachment of a biotin-fluorochrome MSAP to proteins, Garanger, (2009) Bioconj Chem. 20(1) 170. Currently, the attachment of non-fluorescent functionalities, such as chelates or biotin, to a substrate can only be monitored by complex, insensitive or inaccurate methods of analytical chemistry. The absorbance of NBD was used to monitor the reaction of an MSAP with an RGD substrate as shown in FIG. 4D. The absorbance of CYAL-5.5 was used to monitor the attachment of an MSAP to annexin (FIG. 11).

Yet another problem addressed by MSAPs is the fate of gold nanoparticles in biological systems. Gold nanoparticles are instable in physiological buffers, and tend to aggregate and precipitate in saline rich environments. By using MSAPs, a stabilizing ethyleneglycol polymer (F1) can be coated onto the surface of gold nanoparticles. The simultaneous conjugation of a metal chelate (F2) and a fluorochrome (F3) enables multimodal detection and imaging possibilities.

Therefore, the invention provides a method for preparing a multifunctional probe. In the method, a first functional group and a second functional group are attached to a peptide scaffold to create a reagent having an attached first functional group, an attached second functional group, and a reactive group. The reagent is then attached to a substrate by reaction of the reactive group with a complementary reactive group of the substrate.

In the method, the reagent is prepared to yield a predetermined stoichiometric ratio of the first functional group and the second functional group on the scaffold such that the probe has a fixed stoichiometric ratio of the first functional group and the second functional group. One non-limiting example for the predetermined stoichiometric ratio for the first functional group and the second functional group is 1:1. However, other ratios for the stoichiometric ratio for the first functional group and the second functional group are possible, and when using three or more functional groups, other ratios are possible. For example, if the first functional group attaches to a first residue of the peptide scaffold and the second functional group attaches to a second different residue of the peptide scaffold, the stoichiometric ratio for the first functional group and the second functional group in the peptide scaffold can be controlled by controlling the ratio of the number of first residues and the number of second residues in the peptide scaffold. Thus, the invention addresses the problem of non-stoichiometric functional group attachment in prior compositions.

The peptide scaffold can include any number of residues; however, for ease of synthesis and reproducibility in clinical trials, it is preferred to limit the residues in the peptide to 20 or less, more preferably, 10 or less, more preferred 5 or less, and most preferred 3 or less. Also, it can be preferred to include at least two different residues in the peptide to provide alternative attachment points for the first functional group and the second functional group. The peptide can include a residue having a nitrogen containing side chain. The peptide can include a lysine residue and/or a cysteine residue. However, other amino acid residues can comprise the peptide. The peptide can include a spacer residue (e.g., alanine or other amino acids) that is not attached to the first functional group or the second functional group or any other functional group. The peptide can include a charged residue.

The invention also provides another method for preparing a multifunctional probe. In this method, a first peptide scaffold and a second peptide scaffold are used. The first peptide scaffold can be the same as the second peptide scaffold. A first functional group is attached to the first peptide scaffold, and a second functional group is attached to the second peptide scaffold. The second functional group is different from the first functional group. A third functional group is attached to the first peptide scaffold of the first reagent to create a first reagent having an attached first functional group and an attached third functional group. A fourth functional group is attached to the second peptide scaffold of the second reagent to create a second reagent having an attached second functional group and an attached fourth functional group. The third functional group can be the same or different from the fourth functional group. The first reagent can be attached to a substrate by reaction of a reactive group of the first reagent with a complementary reactive group of the substrate. The reactive group of the first reagent and the complementary reactive group of the substrate can be the single attachment point for the first peptide scaffold and the substrate. In one version of this method, the reactive group is attached to the first reagent, and thereafter the reactive group of the first reagent may be reacted with the complementary reactive group of the substrate. This method provides a divergent synthetic strategy yielding multiple MSAPs from a common peptide scaffold.

The invention also provides a kit for preparing a multifunctional probe. The kit includes a reagent comprising (i) a plurality of peptide scaffolds, each scaffold having a reactive group, (ii) a first functional group attached to each scaffold, and (iii) a second functional group attached to each scaffold wherein the second functional group is different from the first functional group. The kit further includes a substrate having a complementary reactive group suitable for reacting with the reactive group of each scaffold. The reagent of the kit is prepared to yield a predetermined stoichiometric ratio of the first functional group and the second functional group on each scaffold such that a probe having a fixed stoichiometric ratio of the first functional group and the second functional group on the substrate can be formed by reacting the reactive groups of peptide scaffolds with the complementary reactive groups on the substrate. When a plurality of peptide scaffolds is provided in the reagent of the kit (or the reagent is provided without the substrate of the kit), it can be advantageous to provide peptide scaffolds of the same predetermined molecular weight to aid in reproducibility in clinical trials. The addresses the problems associated with multiple molecular weights in prior synthetic polymer scaffolds.

The invention also provides a method for medical imaging a patient. In the method, a multifunctional probe is administered to a patient. The multifunctional probe includes a substrate attached to a plurality of peptide scaffolds. Each scaffold has an attached first functional group and an attached second functional group wherein the second functional group is different from the first functional group and wherein each scaffold has the same molecular weight. Imaging is performed using a first imaging method by detecting a first signal from the multifunctional probe, and imaging is performed using a second imaging method by detecting a second signal from the multifunctional probe. The first imaging method and the second imaging method can each be selected from positron emission tomography, single-photon emission computed tomography, magnetic resonance imaging, computerized tomography, optical imaging, and ultrasound.

The invention also provides a method for monitoring the extent of attachment of first functional groups to a substrate. In the method, a first functional group and a second functional group are attached to a plurality of peptide scaffolds to create a plurality of reagents having an attached first functional group, an attached second functional group, and a reactive group. A number of the plurality of reagents are attached to the substrate by reaction of the reactive group of each of the number of the plurality of reagents with a surface of the substrate to create a modified substrate having first functional groups and second functional groups. An intensity of emitted energy from second functional groups on the substrate is measured, and an amount of first functional groups on the substrate is calculated based on the measured intensity of emitted energy from second functional groups on the substrate. The reagents can be prepared to yield a predetermined stoichiometric ratio of the first functional group and the second functional group on each peptide scaffold such that the substrate modified with the scaffold has a fixed stoichiometric ratio of the first functional group and the second functional group.

These and other features, aspects, and advantages of the present invention will become better understood upon consideration of the following detailed description, drawings, and appended claims.

DETAILED DESCRIPTION OF THE INVENTION

Figure 1:
FIG. 1 shows strategies to obtain multifunctional probes and the design of multifunctional single-attachment-point reagents (MSAPs). In a), a prior art multifunctional probe can be obtained when a substrate is reacted with two chemically reactive functional groups in sequential fashion where $F^1$=Functional Group 1 and $RG^1$=Reactive Group 1. In b), a probe of the invention is made. Here a substrate can be reacted with an MSAP reagent to obtain a multifunctional probe in single step. In c), a bifunctional MSAP peptide scaffold consists of a Lys-Cys dipeptide to which two functional groups, $F^1$ and $F^2$, are attached. In d), a trifunctional MSAP peptide scaffold consists of a Lys-Lys-βAla-Cys tetrapeptide to which three functional groups, $F^1$, $F^2$ and $F^3$, are attached. A "probe" includes a "substrate" modified by one or more "functional groups".
Figure 1:
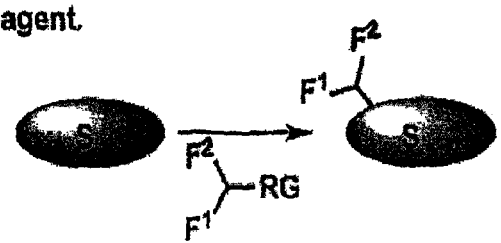
Figure 1:
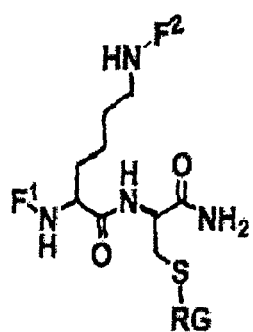
Figure 1:
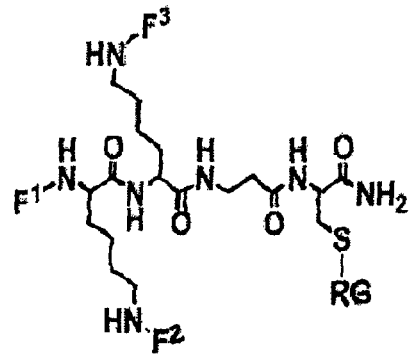

The need for multifunctional probes, together with the limitations of current syntheses, led us to develop of a new class of reagents designed for the simplified and reproducible syntheses of multifunctional probes. We have termed such compounds "multifunctional single attachment-point" (MSAP) reagents. To obtain multifunctional probes using the methods of the invention, a substrate is reacted with a multifunctional single-attachment-point (MSAP) reagent. The MSAP reagents can include three components: (i) a peptide scaffold, (ii) two or more functional groups (denoted $F^1$, $F^2$, $F^3$, $F^n$, etc.), (iii) a single chemically reactive group (RG) for reaction of the MSAP with a substrate containing a complementary reactive group.

Non-limiting examples of functional groups (which can belong to diverse classes of molecules) for use in the MSAP reagents are summarized in Table 1 below. Functional groups are of certain general types. Some permit detection of the probe (fluorochromes, chelates, biotin). Some change the physical properties of the probe (polymers, charged groups). Some add a physiological activity to the MSAP and consequently to the probe (membrane translocating peptides, SiRNA, wortmannin, methotrexate).

TABLE 1

Examples of functional groups ($F^1$, $F^2$, $F^3$, $F^n$) for MSAPs

| Functional Group | Type | Comment |
|---|---|---|
| Coumarins | Fluorochrome | Absorption ~350 nm |
| Fluoresceins | Fluorochrome | Absorption ~500 nm |
| Rhodamines | Fluorochrome | Absorption ~550 nm |
| Cyanine dyes | NIR Fluorochrome | Absorption >650 nm For in vivo imaging |
| Phenol | | For (radio)iodination |
| Diethylene triamine pentaacetic acid (DTPA) | Metal chelate | Chelation of radioactive metals or magnetic metals |
| Tetraazacyclododecane tetraacidic acid (DOTA) | Metal chelate | Chelation of radioactive metals or magnetic metals |
| Biotin | Immunoreactive hapten | Avidin detection |
| poly(ethylene glycol) (PEG) | Neutral polymer | Increase MW, change physical properties |
| Dextran | Polymer | Increase MW, change physical properties |
| Protamine | Polymer | Add Positive charge, add membrane translocating Ability |
| Polyarginine | Polymer | Add Positive charge, add membrane translocating Ability |
| Si RNA | Therapeutic agent | Therapeutic effect |
| Methotrexate | Therapeutic agent | Therapeutic effect |
| Paclitaxel | Therapeutic agent | Therapeutic effect |
| Doxirubicin | Therapeutic agent | Therapeutic effect |
| Wortmannin | Therapeutic agent | Therapeutic effect |

Non-limiting examples of reactive groups for use in the MSAP reagents are listed in Table 2 below. It can be appreciated from Table 2 that as used herein, the term "complementary reactive group" can include a group of atoms (e.g., amine) or a single atom (e.g., gold).

TABLE 2

Examples of reactive groups (RG)

| RG on MSAP | Complementary reactive group on Substrate |
|---|---|
| N-hydroxysuccinimide (NHS) ester | amine |
| maleimide | thiol |
| thiol | gold surface (Au) |
| thiol | maleimide |
| alkyne | azide |
| azide | alkyne |
| aldehyde | oxyamine, hydrazide |

Non-limiting examples of substrates to which the MSAP reagents can be attached are listed in Table 3 below. The substrate (S) can be low molecular weight molecule, a protein, a nanoparticle or a surface of a device which presents a chemistry enabling reaction with the reactive group (RG) of the MSAP. Since MSAP's have been used for surface modification of a gold nanoparticle, see Example 4, they can be used to modify any surface which provides a chemistry that reacts with the reactive group (RG) of the MSAP. Thus, a substrate could be a silanized glass slide, gold nanowire, or a micron-size magnetic bead.

TABLE 3

Examples of Substrates (S) to react with MSAPs

| Substrate Class | Examples |
|---|---|
| Nanoparticles | Magnetic iron oxides, gold, quantum dots |
| Proteins | Annexin V, single chain antibodies, antibodies, nanobodies |

TABLE 3-continued

Examples of Substrates (S) to react with MSAPs

| Substrate Class | Examples |
|---|---|
| Polymers | Polylysine, dextran |
|  | Polyamino acids, polysaccharide |
| Enzymes |  |
| Cyclic peptides | Cyclo[-RGDfK-] |
| Linear peptides | Peptides with a single chemically reactive group distant from those involved in biological activity, e.g., the N-terminal group of bombesin-like peptides |
| Drugs | Mitomycin C, methotrexate, doxorubicin, paclitaxel |
| Vitamins | Folic acid, Vitamin B12 |
| Macroscopic device surface | Silanized class surface, polystyrene, polypropylene, |

MSAPs can include multiple functional groups ($F^1$, $F^2$, $F^3$, $F^n$, etc.), a reactive group (RG), and a peptide scaffold (PS).

The MSAP concept is shown schematically in FIG. 1 b), c) and d). An MSAP featuring various functional groups ($F^1$, $F^2$) and a single chemically reactive group (RG) is reacted with a substrate, to obtain a multifunctional probe in one step. Functional groups can be, for example, chelates, fluorochromes, polymers, affinity tags. MSAP reagents are based on peptide scaffolds to which the different functional groups and a single reactive group are attached. See FIG. 1 c) and d). Bifunctional MSAPs employed a Lys-Cys scaffold for the presentation of two functional groups ($F^1$, $F^2$) (FIG. 1 c)), while trifunctional MSAPs ($F^1$, $F^2$, $F^3$) were built on a Lys-Lys-βAla-Cys scaffold (FIG. 1 d)). The syntheses of a bifunctional MSAP and of a trifunctional MSAP are given in FIGS. 2 and 3, respectively, and an example of their application for molecular imaging and nanoparticle surface chemistry is provided in FIGS. 4 and 5, respectively.

Figure 2:
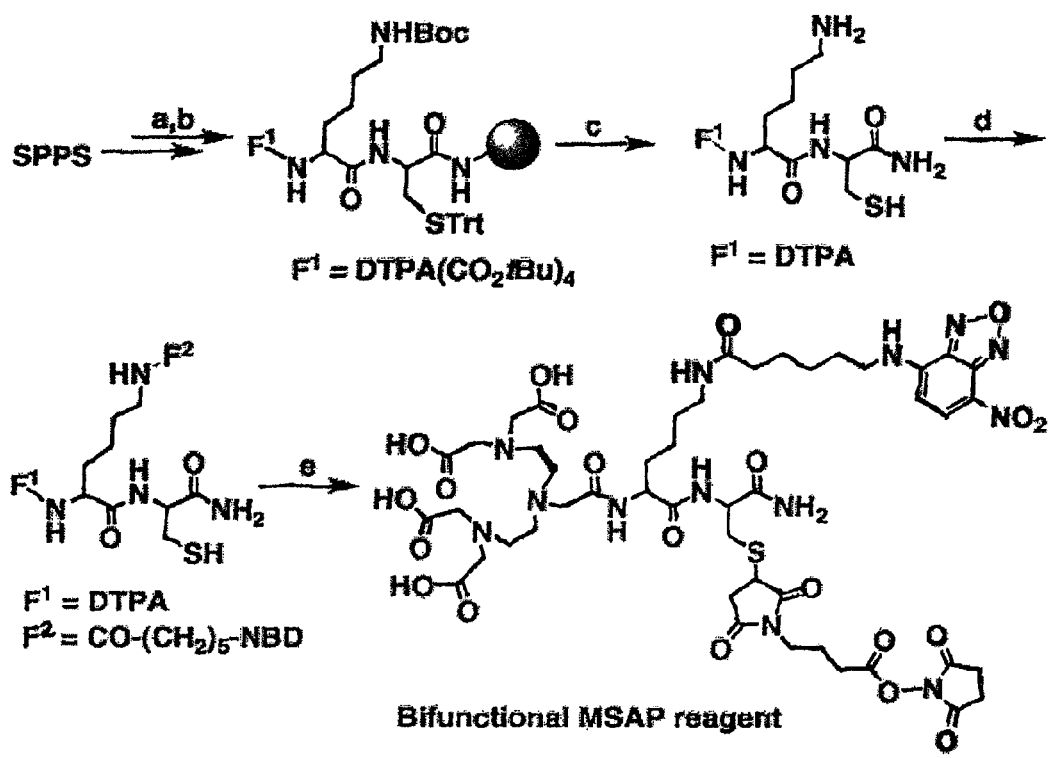
FIG. 2 shows a synthesis scheme for a bifunctional MSAP reagent.

A bifunctional MSAP ($F^1$=DTPA derivative for metal chelation, $F^2$=NBD fluorochrome (7-nitrobenz-2-oxa-1,3-diazol-4-yl), RG=NHS ester) was prepared as shown in FIG. 2. A partially protected DTPA derivative, diethylenetriamine-N,N,N'',N'''-tetra-tert-butyl acetate-N'-acetic acid (DTPA($CO_2tBu$)$_4$), was reacted at the N-terminus of the Lys(Boc)-Cys(Trt) sequence on a solid support (steps a and b). After full deprotection and cleavage (step c), the differential reactivity of the primary amine and thiol groups of the DTPA-Lys-Cys intermediate enabled two consecutive site selective reactions in solution. An NHS ester activated NBD derivative was firstly attached to the lysine side chain (step d). Finally, a commercially available thiol to amine crosslinking agent maleimidobutyryloxy-succinimide ester, step e) was reacted with the thiol group of the cysteine to endow the bifunctional MSAP with an NHS ester reactive group.

Figure 3:
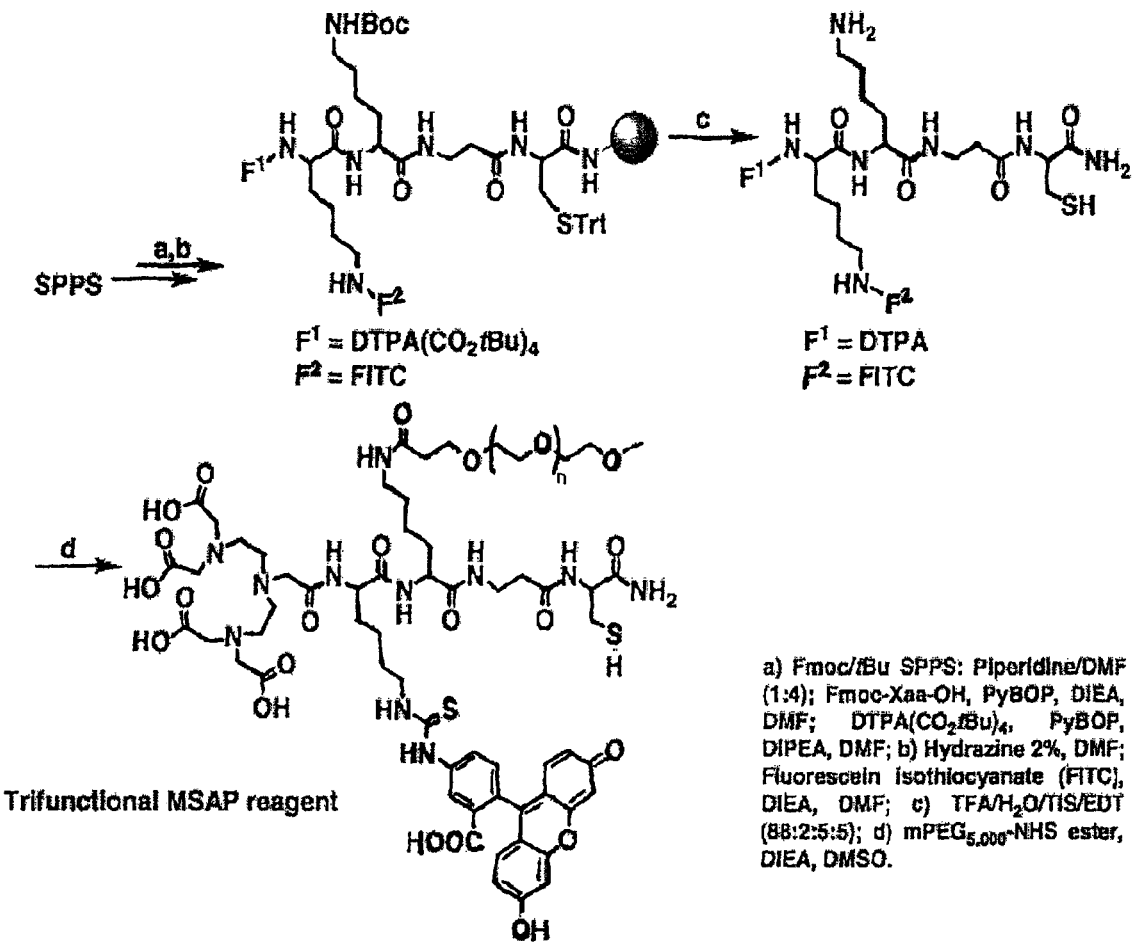
FIG. 3 shows the synthesis scheme for a trifunctional MSAP reagent.
Figure 4:
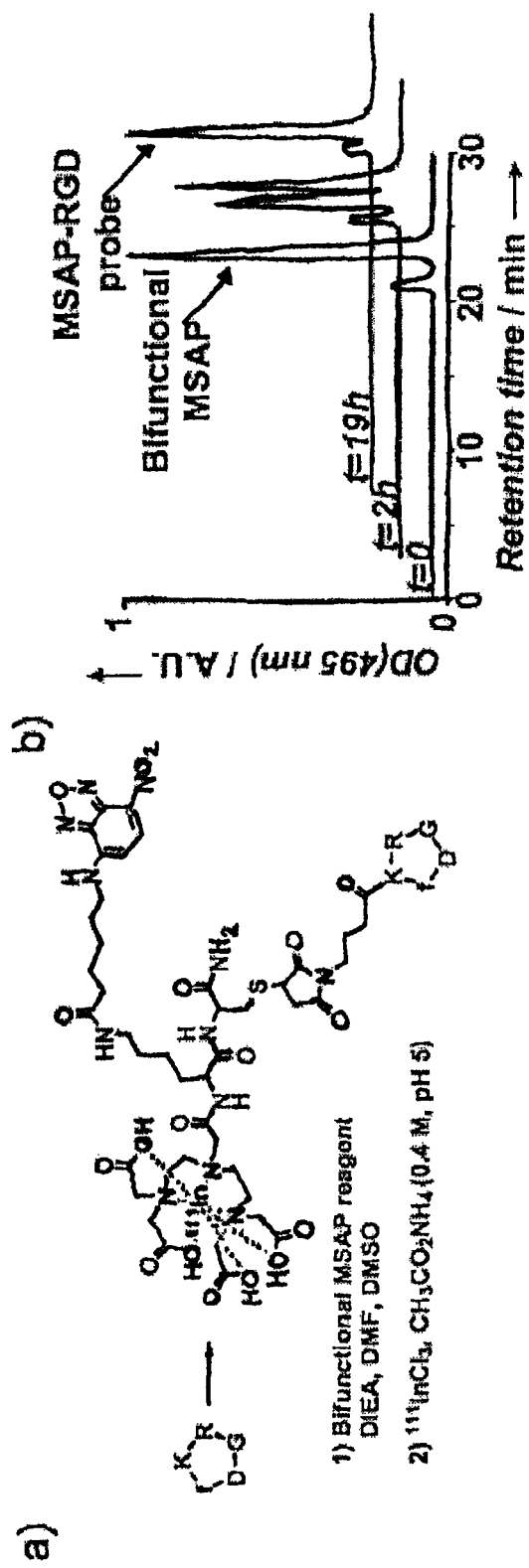
FIG. 4 shows molecular imaging with a bifunctional MSAP-RGD probe. In a), the bifunctional MSAP (see FIG. 2) was attached onto the lysine side chain of the cyclo[-RGDfK-]tumor-targeting peptide. In b), the reaction between the bifunctional MSAP and the RGD substrate was monitored by RP-HPLC using NBD's absorbance. In c), after complexation with $^{111}InCl_3$, the bifunctional MSAP-RGD probe was injected into a tumor-bearing mouse and monitored by SPECT-CT. In d), the distribution of the probe within the tumor was visualized by immunohistochemistry with an antibody to the NBD hapten and compared to the distribution of CD31 (marker for endothelial cells) and CD11b (marker for monocytes/macrophages).
Figure 4:
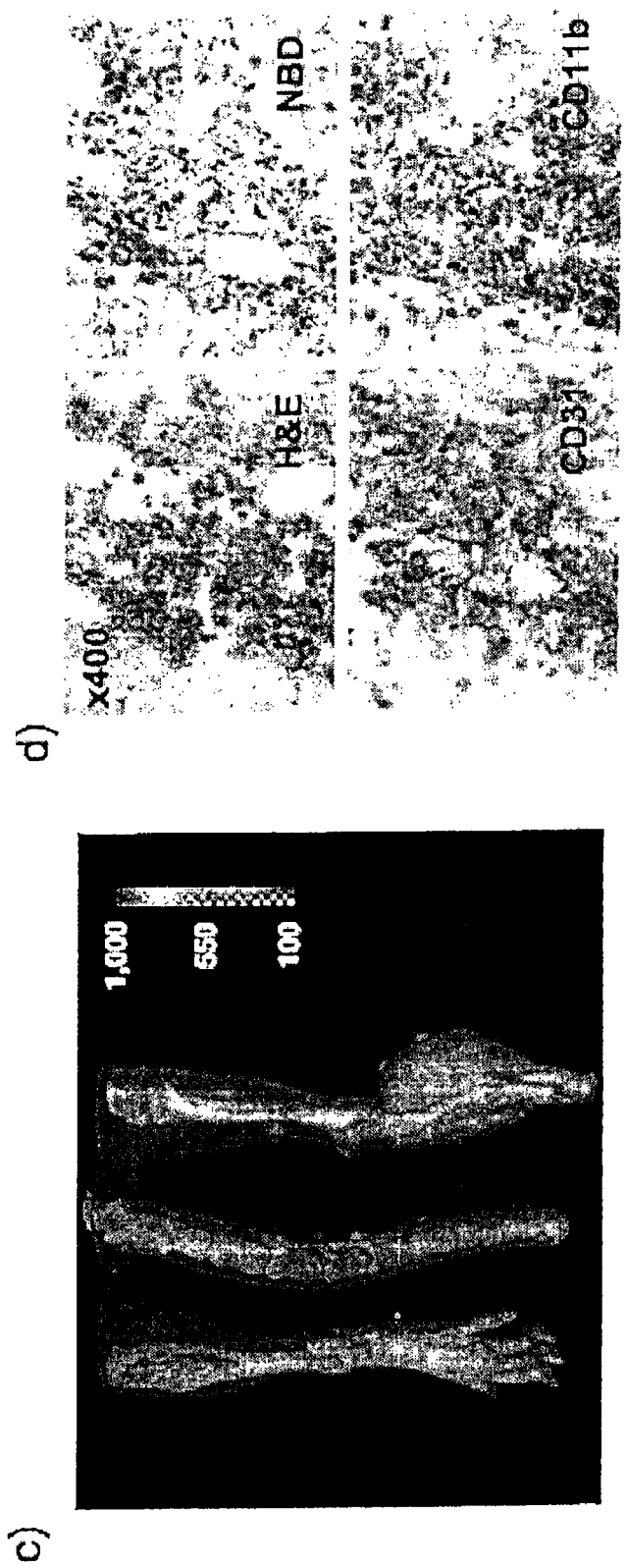

A trifunctional MSAP ($F^1$=chelate, $F^2$=fluorescein, $F^3$=PEG, RG=thiol) was synthesized as shown in FIG. 3. DTPA($CO_2tBu$)$_4$ was again reacted at the N-terminus of the Lys(ivDde)-Lys(Boc)-βAla-Cys(Trt) sequence on a solid support (step a). FITC was attached after selective removal of the ivDde protecting group (step b). After cleavage and deprotection (step c), the DTPA-Lys(FITC)-Lys-βAla-Cys intermediate was reacted with a 5 kDa NHS ester-activated methoxypolyethyleneglycol.

To demonstrate the advantage of the bifunctional MSAP reagent, we used as a model substrate the cyclo[-RGDfK-] peptide currently exploited for its high affinity for integrins (see, Haubner et al., J Nucl Med (1999) 40:1061-1071). The latter presents a single modifiable amine outside the —RGD-binding motif. The bifunctional MSAP (FIG. 2) was then reacted with the peptide to obtain in one step the bifunctional probe (FIG. 4 a)). NBD's absorbance allowed ready monitoring of the reaction by HPLC (FIG. 4 b)). After the chelation of $^{111}$In, the MSAP-RGD probe was administered intravenously to a mouse bearing an integrin-expressing B16F0 melanoma (see Sancey et al., Eur J NuclMed Mol Imaging (2007) 34:2037-2047) and the probe disposition was determined by SPECT-CT (FIG. 4 c)). To visualize the distribution of the MSAP-RGD probe within the tumor, an antibody to the NBD hapten was employed. Accumulation of the MSAP-RGD probe occurred in parts of the tumor with high CD31 (endothelial cell maker) levels and CD11b (monocytes/macrophages marker) levels (FIG. 4 d)). Thus, a peptide featuring a single modifiable center was reacted with the MSAP to provide, in only one synthetic step, a probe whose disposition could be monitored concurrently by two modalities: tumoral uptake and gross tumor distribution were determined by SPECT and disposition within the tumor tissue was determined by immunohistochemistry. Since both tumor and endothelial cells express RGD binding integrins (see Pasqualini et al., Nat Biotechnol (1997)15: 542-546; and Brooks et al., Cell (1994) 79:1157-1164), the association of the probe with endothelial cell-rich areas suggests that tumor-associated radioactivity results from the binding of the probe to endothelial cell rather than tumor cell integrins.

Figure 5:
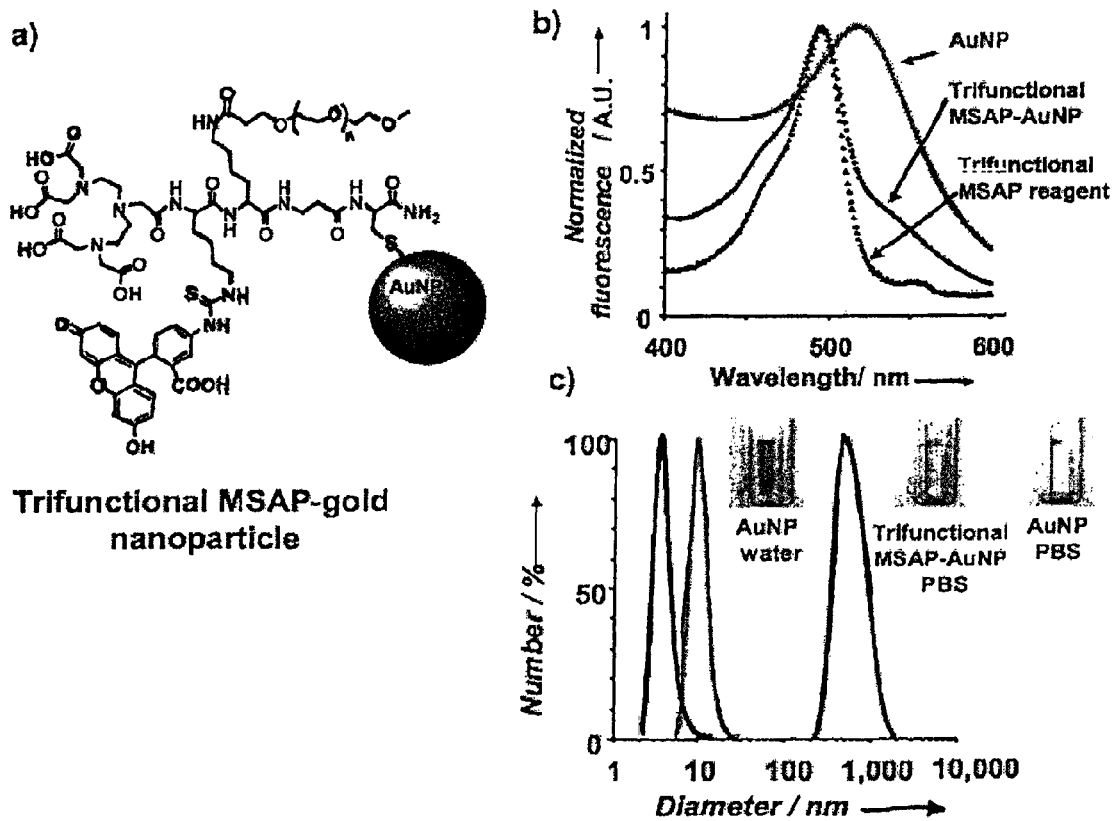
FIG. 5 shows gold nanoparticle modification and stabilization with a trifunctional MSAP reagent. In a), the trifunctional MSAP (see FIG. 3) was reacted to the surface of a gold nanoparticle (AuNP) to obtain a trifunctional MSAP-AuNP probe. In b), there is shown absorption spectra of the trifunctional MSAP reagent, AuNP and the trifunctional MSAP-AuNP probe. The latter presents absorption maxima at 494 nm (fluorescein isothiocyanate—FITC) and 517 nm (AuNP). In c), the poly(ethylene glycol) (PEG) functional group of the trifunctional MSAP-AuNP stabilized the nanoparticles in physiological buffer as measured by light scattering.
Figure 6:
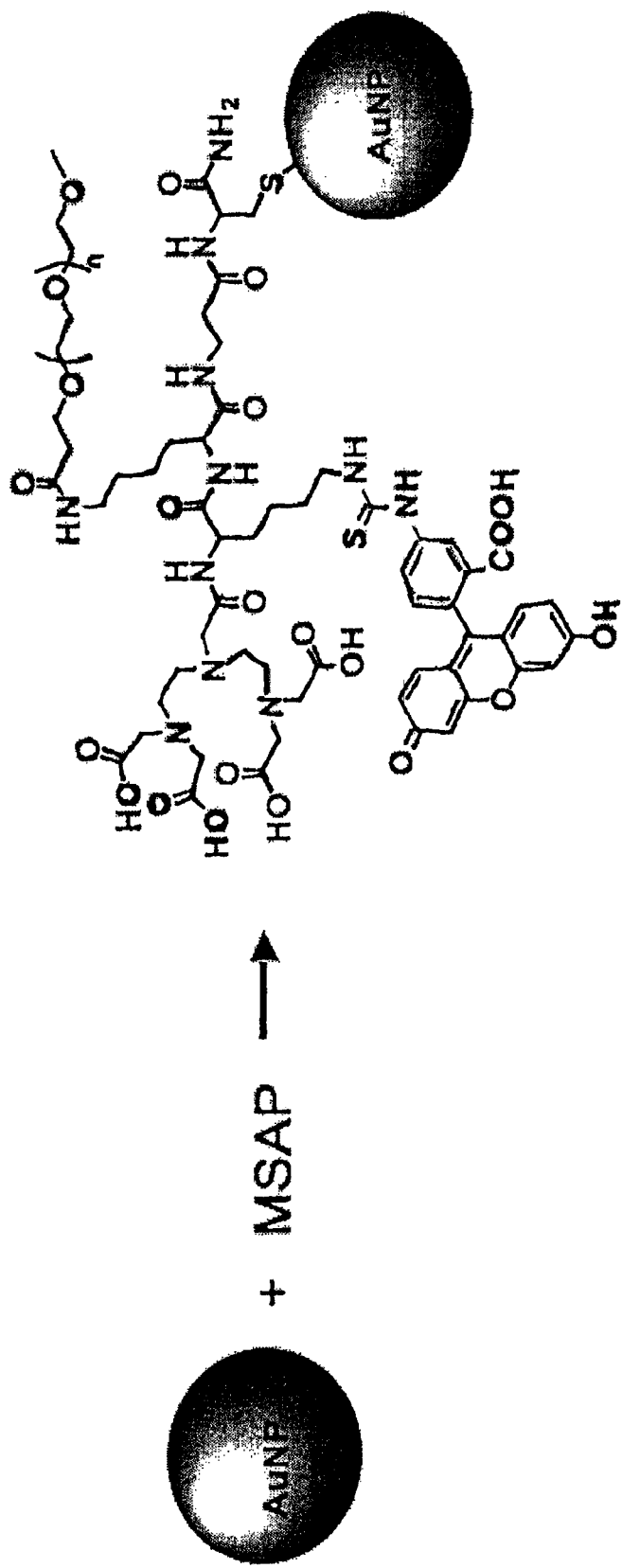
FIG. 6 shows that a nanomaterial, such as a gold nanoparticle (AuNP), can be reacted with a trifunctional, single-attachment-point reagent to obtain a multifunctional probe in a single step.

The utility of the trifunctional MSAP (FIG. 3) for nanoparticle surface design was demonstrated by coating gold colloids (AuNP), as shown on FIG. 5 a). The thiol reactive group RG of the MSAP was reacted with the surface of gold nanoparticles, since thiols react strongly with this surface (see Oliver, Methods Mol Biol (1999) 115:331-334). Here the MSAP provided two functional groups (DTPA, fluorescein) for detection and one for stabilization (PEG). By fluorescein absorbance (FIG. 5 b)), there were 410 MSAPs per nanoparticle. The increased stability of the nanoparticle in PBS due to MSAP attachment is shown in FIG. 5 c). While uncoated nanoparticles aggregated in PBS (size increased from 4.1 nanometers to 500 nanometers after 2 hours), the 10 nanometer MSAP-AuNP remained stable for up to three days.

While most functional group(s), singly or in combination, can be attached to peptide scaffolds to obtain MSAP reagents (FIG. 1 c) and d)), our experience was that certain functional groups may be preferred. When attaching functional groups to the solid phase peptide, functional groups with multiple chemically reactive centers are less preferred since they may crosslink peptides; hence, we employed DTPA($CO_2tBu$)$_4$ rather than DTPA or DTPA anhydride. Second, the functional groups must survive the harsh conditions of peptide deprotection and release. Near infrared fluorochromes may lack the necessary stability to survive the harsh conditions of deprotection and cleavage from a solid support and therefore must be attached to peptide scaffold under mild conditions, after it has been released from the solid support. Fluorescein survives these harsh conditions and can be attached to the peptide when it is attached to the solid support. After cleavage and deprotection, the peptide intermediates obtained (DTPA-Lys-Cys or DTPA-Lys(FITC)-Lys-βAla-Cys) offered a single primary amine and a single thiol, allowing two additional chemoselective reactions in solution. Finally, solid phase peptide scaffolds were manually synthesized on a scale sufficient (0.2-0.5 mmol) to permit the use of peptide intermediates for the preparation of multiple MSAPs from a common intermediate. This afforded a labor savings and gave considerable flexibility to MSAP reagent design. Our preferred MSAP synthetic strategy was therefore to attach robust functional groups to the solid phase peptide, and complete the synthesis with solution phase reactions run under mild conditions.

The advantages of MSAPs for the synthesis of multifunctional probes (fixed functional group stoichiometry, multimodal detection in biological systems, multifunctional modification of substrates bearing a single reactive group, facile monitoring of chemical reactions), can lead to the efficient and reproducible design of ever more complex multifunctional nanomaterials.

The invention is further illustrated in the following Examples which are presented for purposes of illustration and not of limitation.

EXAMPLES

Materials and Methods

Protected L amino acids and PyBOP were obtained from Novabiochem (EMD Biosciences). Other sources were: DTPA(CO$_2$tBu)$_4$ (Macrocyclics), N-[g-maleimidobutyryloxy] succinimide ester (Pierce), succinimidyl 6-(N-(7-nitrobenz-2-oxa-1,3-diazol-4-yl)amino)hexanoate (Invitrogen), and mPEG-NHS ester (5 kDa) (Nanocs Inc).

RP-HPLC (Varian ProStar detector and delivery modules) employed an eluant A (0.1% TFA/water) and eluant B (0.1% TFA in 9.9% water in acetonitrile). An analytical method (Microsorb 100 Å 5 μm C18 particles, 250×4.6 mm$^2$ column and Metaguard 100 Å 5 μm C18 particles 10×4.6 mm$^2$) employed 1 mL·min$^{-1}$ with a linear gradient for 30 minutes. A semi-preparative method (Vydac 300 Å 10 μm C18 particles, 250×22 mm2) employed 20 mL·min$^{-1}$ with a linear gradient for 30 minutes. MS-ESI was done a Micromass (Waters) and MALDI-TOF analyses at the Tufts University Core Facility.

Bifunctional MSAP Synthesis Example 1

DTPA-NBD-NHS Ester Reagent (F$^1$=DTPA, F$^2$=NBD, RG=NHS Ester)

The DTPA(CO$_2$tBu)$_4$-Lys(Boc)-Cys(Trt) peptide was manually synthesized on Rink Amide MBHA resin (0.25 mmol) (EMD Biosciences) with an Fmoc/tBu strategy using a polypropylene 5-mL disposable syringe fitted with a sintered frit. Coupling reactions employed 2 equivalents (relative to resin) of N-α-Fmoc-protected amino acid) activated in situ with 2 equivalents of PyBOP and 3-4 equivalents of DIEA in DMF (10 mL/g resin) for 30 minutes. Coupling efficiency was assessed with trinitrobenzylsulfonyl. N-α-Fmoc groups were removed with a piperidine/DMF solution (1:4) for 10 min (10 mL/g resin). N-ε-ivDde groups were removed with 2% hydrazine in DMF for 5 minutes (10 mL/g resin). The deprotected DTPA-Lys(H)-Cys(H)—NH$_2$ intermediate was released from the solid support with TFA/H$_2$O/TIS/EDT 88:2:5:5 (twice, 2 h, 20 mL/g resin) precipitated and triturated with ether, and dissolved in water. The aqueous layer was washed three times with dichloromethane and lyophilized to yield a white powder (155.0 mg, quantitative yield). Mass spectrum: C$_{23}$H$_{41}$N$_7$O$_{11}$S; MW: 623.7 g·mol$^{-1}$; calculated exact mass: 623.3. found m/z: [M+H]$^+$=624.2, [M−H]$^-$=622.1.

To obtain the bifunctional MSAP, succinimidyl 6-(N-(7-nitrobenz-2-oxa-1,3-diazol-4-yl)amino)hexanoate (5.2 mg, 13.3 μmol, 0.5 equiv.) in 400 μL anhydrous DMF was added to DTPA-Lys(H)-Cys(H)—NH$_2$ (15.3 mg, 24.5 μmol). DIEA (21 μL, 120.6 μmol, 4.9 equiv.) was added and the reaction mixture was stirred for 2 hours at room temperature. After RP-HPLC 90 purification (UV monitoring at 495 nm, 20-60% eluant B in 30 min gradient), the fraction collected (t$_R$=7.7 min) was lyophilized. DTPA-Lys(NBD)-Cys(H)—NH$_2$ (9.1 mg, 10.1 μmol, 76% yield) was obtained as an orange powder. Mass spectrum: C$_{35}$H$_{53}$N$_{11}$O$_{15}$S; MW: 899.9 g·mol$^{-1}$; calculated exact mass: 899.3. found m/z: [M+H]$^+$=899.9, [M+Na]$^+$=921.8, [M+K]$^+$=937.8, [M−H]$^-$95=898.1. Analytical RP-HPLC: 495 nm, 5% eluant B in 5 min, 5-60% eluant B in 30 min, t$_R$=27.4 min. A solution of N-[g-maleimidobutyryloxy]succinimide (MBS) ester (11.7 mg, 41.8 μmol, 4.1 equiv.) in 400 μL anhydrous DMF was added to a solution of DTPA-Lys(NBD)-Cys(H)—NH$_2$ (9.1 mg, 10.1 μmol) in 400 μL 100 anhydrous DMF containing DIEA (5 μL, 28.7 μmol, 2.8 equiv.). The reaction mixture was stirred for 4 hours at room temperature. After RP-HPLC purification (UV monitoring at 495 nm, 20-60% eluant B in 30 min gradient), the fraction collected (t$_R$=12.8 min) was lyophilized. DTPA-Lys(NBD)-Cys(NHS ester)-NH$_2$ (9.7 mg, 8.2 μmol, 81% yield) was obtained as an orange powder. Mass spectrum: C$_{47}$H$_{65}$N$_{13}$O$_{21}$S; MW: 1180.2 g·mol$^{-1}$; calculated exact mass 1179.4. found m/z: [M+H]$^+$=1180.0, [M+Na]$^+$=1201.9. Analytical RP-HPLC: 495 nm, 5% eluant B in 5 min, 5-60% eluant B in 30 min, t$_R$=30.7 min.

Bifunctional MSAP Synthesis Example 2

Biotin-Fluorescein-Maleimide Reagent (F$^1$=Biotin, F$^2$=Fluorescein, RG=Maleimide)

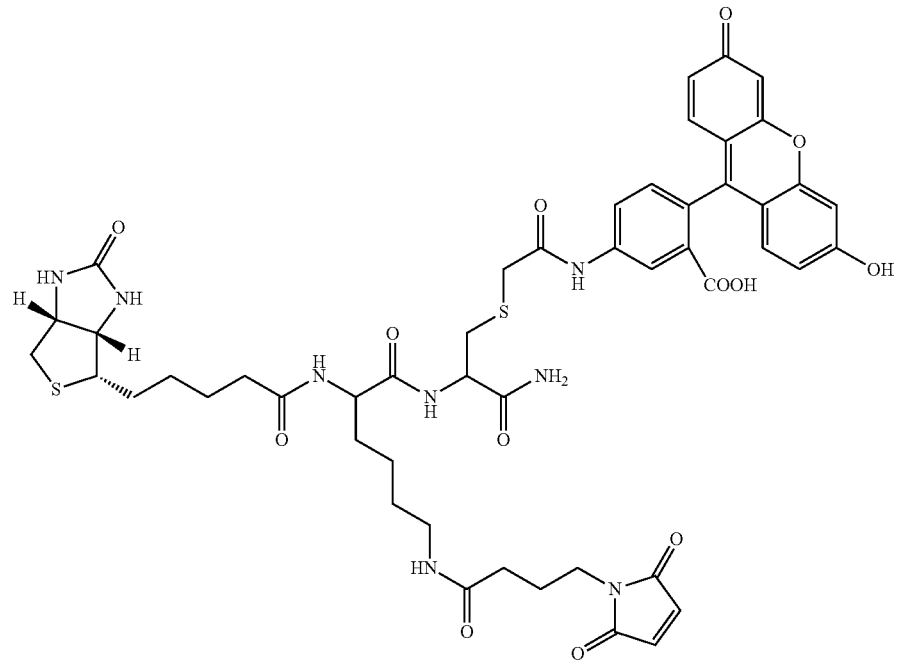 [SMILES: NC(=O)C(CSCC(=O)Nc1ccc(-c2c3ccc(=O)cc-3oc3cc(O)ccc23)c(C(=O)O)c1)NC(=O)C(CCCCNC(=O)CCCN1C(=O)C=CC1=O)NC(=O)CCCC[C@@H]1SC[C@@H]2NC(=O)N[C@@H]21]

biotin-K(maleimide linker)-C(fluorescein)-NH$_2$

Synthesis of the biotin-K(maleimide linker)-C(fluorescein)-NH$_2$

The linear biotin-K(Boc)-C(Trt) sequence was elongated onto the Rink Amide MBHA resin using Solid Phase Peptide Synthesis (Fmoc/t-Bu strategy). The fully deprotected biotin-K(H)—C(H)—NH$_2$ peptide was released from the solid support and obtained as a white powder after lyophilization. Mass spectrum: C$_{19}$H$_{34}$N$_6$O$_4$S$_2$; calc. exact mass: 474.2. found m/z: [M+H]$^+$=475.1.

Solutions of biotin-K(H)—C(H)—NH$_2$ (12.1 mg, 25.5 μmol) in 510 mL anhydrous DMF, fluorescein-5-iodoacetamide (8 mg, 15.5 μmol, 0.6 equiv.) in 155 μl anhydrous DMF and DIEA (5 μL, 28.7 μmol, 1.1 equiv.) were together mixed overnight at room temperature The reaction mixture was purified by RP-HPLC (440 nm, 20% B 10 min-20-60% B 30 min) and the fraction collected (28.7 min) was lyophilized. Biotin-K(H)—C(fluorescein)-NH$_2$ (8.4 mg, 9.7 μmol, 63% yield) was obtained as a yellow powder. Mass spectrum: C$_{41}$H$_{47}$N$_7$O$_{10}$S$_2$; MW: 862.0 g·mol$^{-1}$; calc. exact mass: 861.3. found m/z: [M+H]$^+$=862.0. Analytical RP-HPLC: 440 nm, 5% B 5 min-5-60% B 30 min, RT=27.4 min.

A solution of GMBS (6.9 mg, 24.6 μmol, 5.1 equiv.) in 246 μL anhydrous DMF was added to a solution of biotin-K(H)—C(fluorescein)-NH$_2$ (4.2 mg, 4.9 μmol) in 240 μL anhydrous DMF containing DIEA (1 μL, 5.7 μmol, 1.2 equiv.). The reaction mixture was stirred overnight at room temperature After RP-HPLC purification (440 nm, 20% B 10 min-20-60% B 30 min), the fraction collected (32.9 min) was lyophilized. Biotin-K(maleimide linker)-C(fluorescein)-NH$_2$ (2.1 mg, 2.0 μmol, 42% yield) was obtained as a yellow powder. Mass spectrum: C$_{49}$H$_{54}$N$_8$O$_{13}$S$_2$; MW: 1027.1 g·mol$^{-1}$; calc. exact mass 1026.3. found m/z: [M+H]$^+$=1027.0, [M+Na]$^+$=1048.9. Analytical RP-HPLC: 440 nm, 5% B 5 min-5-60% B 30 min, RT=29.9 min.

Trifunctional MSAP Synthesis Example 3

DTPA-Fluorescein-PEG$_{5,000}$-Thiol Reagent
(F$^1$=DTPA F$^2$=Fluorescein F$^3$=PEG$_{5,000}$, RG=Thiol)

The DTPA(CO$_2$tBu)$_4$-Lys(ivDde)-Lys(Boc)-βAla-Cys (Trt) peptide was synthesized as above. After selective removal of the ivDde group, fluorescein isothiocyanate (FITC) in DMF was added (overnight, 4° C.). The DTPA-Lys(FITC)-Lys(H)-βAla-Cys(H)—NH$_2$ peptide intermediate was released from the solid support, precipitated and triturated with ether, dissolved in HPLC solvent A (10 mg/mL), and purified by RP-HPLC (UV monitoring at 440 nm, 20-60% eluant B in 30 min gradient). The fraction collected (t$_R$=7.0 min) was lyophilized. The peptide was obtained as a yellow powder (210 mg, 87% yield). Mass spectrum: C$_{53}$H$_{69}$N$_{11}$O$_{18}$S$_2$; MW: 1212.3 g·mol$^{-1}$; calculated exact mass: 1211.4. found m/z: [M+H]$^+$=1212.6, [M+2H]$^{2+}$=607.0, mass spectrometer generated fragments [FITC]$^+$=390.3, [DTPA-Lys-Lys-βAla-Cys-NH$_2$+H]$^+$=823.7, [DTPA-Lys-Lys-βAla-Cys-NH$_2$+2H]$^{2+}$10=412.2.

To obtain the trifunctional MSAP, a solution of mPEG-NHS ester (50 mg, 10 μmol, 0.8 equiv.) in 200 μL anhydrous DMSO was added to DTPA-Lys(FITC)-Lys(H)-βAla-Cys (H)—NH$_2$ (15.9 mg, 13.1 μmol). DIEA (2.3 μL, 13.2 μmol, 1 equiv.) was added and the reaction mixture was stirred for 2 days at room temperature. The reaction mixture was diluted in citric acid (0.1 M, pH 5.7) and separated onto a Biogel P10 column (BioRad, 1.6×16.9 cm$^2$ corresponding to a 34 mL column volume). DTPA-Lys(FITC)-Lys(mPEG)-βAla-Cys (H)—NH$_2$ was released in the first dark yellow fraction (8-13 mL). MALDI-TOF mass spectrum: broad peak 20 around 5,500 Da.

Synthesis of the Bifunctional MSAP-RGD Probe

Solutions of cyclo[-RGDfK-] (8.7 mg, 14.4 μmol, 2 eq) in 290 μL anhydrous DMSO containing DIEA (2.5 μL, 14.4 μmol) and DTPA-Lys(NBD)-Cys(NHS ester)-NH$_2$ (8.2 mg, 7.0 μmol) in 140 μL anhydrous DMF were together mixed overnight at room temperature. The reaction mixture was purified by RP-HPLC (UV monitoring at 495 nm, 20% eluant B in 10 min, 20-80% eluant B in 30 min gradient, 6 L·min$^{-1}$ flow rate). The fraction collected (t$_R$=28.5 min) was lyophilized. The bifunctional MSAP-cyclo[-RGDfK-] conjugate was obtained as an orange powder. Mass spectrum: C$_{70}$H$_{101}$N$_{21}$O$_{25}$S; MW: 1668.7; calculated exact mass 1667.7. found m/z: [M+H]$^+$=1669.7; [M+2H]$^{2+}$=835.4 Analytical RP-HPLC: 495 nm, 20% eluant B in 5 min, 20-80% eluant B in 30 min, t$_R$=21.2 min. $^{111}$InCl$_3$ (Perkin Elmer Life and Analytical Sciences, 3.9 mCi) was diluted with 250 μL ammonium acetate (0.4 M, pH 5) and added to 10.8 μL of bifunctional MSAP-cyclo[-RGDfK-] conjugate (108 μg, 64.7 nmol) in DMSO. The reaction mixture was incubated (1 h, rt) diluted with water (5 mL), and purified on a SepPak tC$_{18}$ cartridge preconditioned with ethanol and deionized water. Unreacted $^{111}$InCl$_3$ was removed by elution with water (5 mL) while the pure radiolabeled probe was released by elution with ethanol (1 mL). The solvent was evaporated by microwave heating at 65° C. under a flow of Argon gas for 5 minutes and the $^{111}$In-MSAPRGD probe (2.4 mCi) was dissolved in 1.21 mL DPBS (2 μCi/μL). An aliquot of the DPBS solution was analyzed by RP-HPLC (eluent A, 0.1% trifluoroacetic acid in water; eluent B, acetonitrile; 5-60% eluant B in 15 min gradient; 1 mL·min$^{-1}$ flow rate) employing a Varian 210 high performance liquid chromatograph with a Varian C18 reversed-phase column (10×250 mm$^2$), a multiwavelength UV detector and a flowthrough gamma detector connected in series. The $^{111}$In-MSAP-RGD probe was found to be 97% radiochemically pure (t$_r$=14.8 min).

Detection of the Bifunctional MSAP-RGD Probe by SPECT and Immunohistochemistry

Approximately 1·10$^6$ B16F0 murine melanoma cells (from C57BL6 mice) in PBS (40 μL) were injected s.c. into the right hind paw of 6-8 weeks female C57BL6 mice (Charles River Laboratories). After 4 weeks, tumors reached a size suitable for nuclear imaging experiments.

SPECT imaging co-registered with high-resolution CT was performed on a X-SPECT™ system (Gamma Medica, Northridge, Calif., USA). The SPECT system has two gamma cameras, equipped with 1 mm diameter medium-energy pinhole collimators. The solid state CT is mounted on the same gantry as the gamma cameras enabling high quality image fusion. The SPECT images were reconstructed using OSEM (ordered subsets expectation maximization) and CT images were reconstructed using a modified Feldkamp cone-beam reconstruction algorithm (COBRA). The $^{111}$In-MSAP-RGD probe (300 μCi in 150 μL) was injected (iv, tail vein) and after 2 hours mice were anesthetized (isoflurane). CT (256 projections, 50 kV, 0.5 mA) was performed followed by a SPECT acquisition with parameters of 64 projections, 30-120 seconds per projection and a radius of rotation of 3.5 cm giving a resolution of 1.8 mm. The SPECT-CT images were reconstructed and registered for exact 3D anatomical localization of the tracer signal. Mean SPECT pixel intensity and tumor volumes were determined by designing regions of interest (ROIs) on the hind paws of the micrometer resolution CT scans and extrapolating these ROIs to the fused SPECT data using Osirix software.

For NBD-immunohistochemistry, tumors were excised, frozen in OCT compound (Sakura Finetek, Tokyo, Japan) and sectioned in 5 μm slices. Sections were then stained with hematoxylin and eosin for overall morphology. For immunohistochemistry, adjacent sections were preincubated with 0.3% hydrogen peroxide to inhibit endogenous peroxidase activity and then incubated with primary polyclonal rabbit anti 4-fluoro-7-nitrobenzofurazan antibody (AbD Serotec), monoclonal CD31 (BD Pharmingen) for microvessel detection and monoclonal CD11b (BD Pharmingen) for detection of monocyte/macrophage infiltration. After washing with PBS, a secondary biotinylated anti-Rat IgG (Vector Laboratories, Inc.) antibody was applied, followed by avidin-peroxidase complex (Vectastain ABC kit; Vector Laboratories). The reaction was visualized with 3-amino-9-ethyl carbazole substrate (AEC; Sigma Chemical Co). Sections were counterstained with Mayer's hematoxylin solution (Sigma) and mounted. Images were captured with a digital camera (Nikon DXM1200-F, Nikon Inc, Melville, N.Y.) using imaging software ACT-1 (version 2.63).

Example 4

Synthesis of Trifunctional MSAP-gold Nanoparticle Probe and its Stabilization

DTPA-Lys(FITC)-Lys(mPEG)-βAla-Cys(H)—NH$_2$ (100 μL, 258 μM) in citric acid (0.1 M pH 5.7) was added to 1000 μL gold colloids (Sigma Aldrich, 66 nM, 78.5 nm$^2$/NP, 5 nm nanoparticles) for 2 hours at room temperature and nanoparticles purified by Sephadex G100.

To obtain the number of MSAPs per nanoparticle, UV/Vis spectra were obtained. The spectra of MSAP-AuNP was treated as the algebraic sum of fluorescein and NP spectra and deconvoluted mathematically to determine the concentrations of MSAP and AuNP. The number of gold atoms per NP was determined from gold concentration and nanoparticle volume.

For stabilization of the nanoparticle with the MSAP, number weight average diameters were obtained by light scattering using a Nano-2S Zetasizer (Malvern Instruments).

Example 5

A Divergent Strategy to Synthesize MSAP Reagents for Protein Conjugation Background for Example 5

The desire for multifunctional nanoparticles, imaging agents and drug delivery systems is a common theme in diverse areas of biology and medicine. Nanoparticles, some polymers, and antibodies feature many reactive groups per mole, and multifunctional probes can be obtained by independently conjugating several monofunctional molecules (e.g. FITC, DTPA anhydride, NHS esters of PEG, etc.). This strategy has been employed (see, for example, Gao et al., (2004) In vivo cancer targeting and imaging with semiconductor quantum dots. *Nat Biotechnol* 22, 969-76; Kircher, Weissleder, and Josephson, (2004) A dual fluorochrome probe for imaging proteases. *Bioconjug Chem* 15, 242-8; and Medarova et al., (2007) In vivo imaging of siRNA delivery and silencing in tumors. *Nat Med* 13, 372-7). However, the use of independent reagents yields multifunctional probes that lack a stoichiometric relationship between the various functional groups attached, since the efficiency of reaction between the substrate and each functional group is independent of the other and each shows some variability. When one considers the design of multifunctional probes using low molecular weight protein substrates, such as annexin V, the attachment of multiple groups at levels greater than about 1 mole per mole of annexin V leads to a loss of bioactivity (see, Schellenberger et al., (2004) Optimal modification of annexin V with fluorescent dyes. *Chembiochem* 5, 271-4). Finally, some low molecular weight substrates like a widely used cyclic RGD peptide (see, e.g., Garanger et al., (2008) Simplified syntheses of complex multifunctional nanomaterials. *Chem Commun (Camb)*, 4792-4), feature only a single chemically reactive group, so that a multiple functional probe can only be obtained by attaching several functional groups to, for example, a single reactive amine or carboxyl group. Thus the design of multifunctional materials of different sizes and types face limitations when multifunctionality is achieved using multiple monofunctional reagents.

Figure 7:
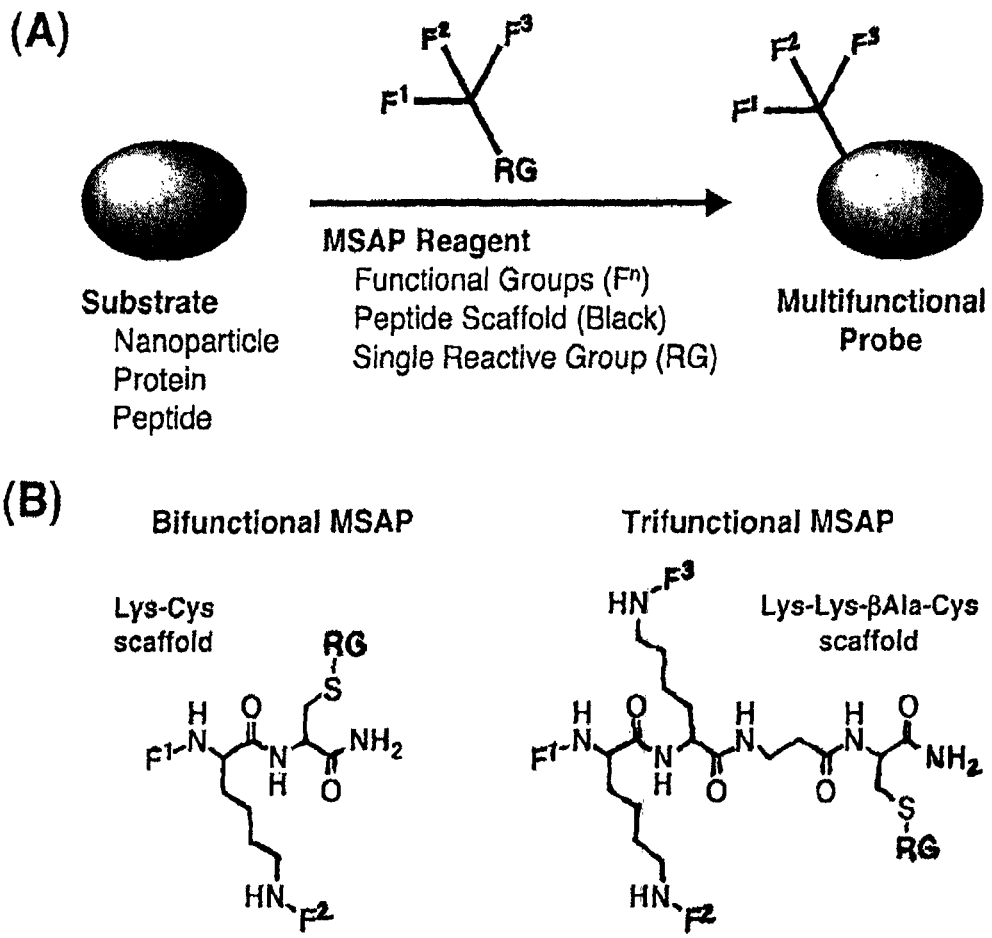
FIG. 7 shows Multifunctional Single-Attachment-Point (MSAP) Reagents, Concept and General Structures. In (A), there is a schematic view of the MSAP concept. An MSAP reagent, composed of three functional groups ($F^1$, $F^2$ and $F^3$) and a reactive group (RG), is reacted with a substrate to yield a multifunctional probe in one reaction step. The substrate can be from different classes of bioactive materials (nanoparticle, polymer, protein, peptide). In (B), bifunctional MSAP reagents consist of two functional groups ($F^1$, $F^2$) and a reactive group (RG) attached to a dipeptide Lys-Cys-$NH_2$ scaffold. Trifunctional MSAP reagents consist of three functional groups ($F^1$, $F^2$, $F^3$) and a reactive group attached to a tetrapeptide Lys-Lys-βAla-Cys-$NH_2$ scaffold.

To overcome these issues, there has been developed multifunctional, single attachment point reagents (MSAP reagents) depicted in FIG. 7. Monofunctional groups ($F^1$, $F^2$) and a reactive group (RG) are attached to a peptide scaffold, and the MSAP reagent is then reacted with a substrate to create a multifunctional probe in a single step.

In Example 5, we demonstrate two advantages of the MSAP reagent approach. Using a divergent synthetic strategy, we show that intermediates in the MSAP syntheses can be split to efficiently yield panels of MSAP reagents. Second, a bifunctional MSAP fluorochrome chelate was synthesized and attached to annexin V, an often-used protein in apoptosis research and in molecular imaging. The MSAP-annexin V featured 0.7 moles of fluorochrome and 0.7 moles of chelator per mole of annexin V. The total number of functional groups (1.4 functional groups per mole of annexin V) had been shown to produce annexin V inactivation (see Schellenberger et al. noted above), but the single attachment point strategy of the MSAP reagent preserved annexin V recognition of apoptotic A549 cells. In this case, a multifunctional annexin V was obtained by utilizing the single attachment point of the bifunctional MSAP reagent.

Experimental Procedures

MSAP Syntheses

Intermediate DTPA-Lys(FI)-Cys-NH$_2$: A solution of 6-(fluorescein-5-carboxyamido)hexanoic acid, succinimidyl ester (10.0 mg, 17.0 μmol, 0.7 equiv.) in 100 μL anhydrous DMSO was added to a solution of DTPA-Lys-Cys-NH$_2$ (15.3 mg, 24.6 μmol) in 250 μL anhydrous DMSO containing DIPEA (12.9 μL, 74.0 μmol, 3 equiv.). The reaction mixture was stirred overnight at room temperature and purified by RP-HPLC. The fraction collected was lyophilized. DTPA-Lys(FI)-Cys-NH$_2$ (10.5 mg, 9.6 μmol, 56% yield) was obtained as a yellow powder. Mass spectrum: $C_{50}H_{62}N_8O_{18}S$; MW: 1095.1 g·mol$^{-1}$; calc. exact mass 1094.4. found m/z: [M+H]$^+$=1095.7, [M+2H]$^{2+}$=548.6.

DTPA-Lys(FI)-Cys(NHS$^a$), (1 in FIG. 8): A solution of N-[g-maleimidobutyryloxy] succinimidyl ester (GMBS, 9.5 mg, 33.9 μmol, 6.6 equiv.) in 400 μL anhydrous DMF was added to a solution of DTPA-Lys(FI)-Cys-NH$_2$ (5.6 mg, 5.1 μmol) in 250 μL anhydrous DMF containing DIPEA (3 μL, 17.2 μmol, 3.4 equiv.). The reaction mixture was stirred overnight at room temperature and purified by RP-HPLC. The fraction collected was lyophilized. DTPA-Lys(FI)-Cys(NHS$^a$) (4.4 mg, 3.2 μmol, 63% yield) was obtained as a yellow powder. Mass spectrum: $C_{62}H_{74}N_{10}O_{24}S$; MW: 1375.4 g·mol$^{-1}$; calc. exact mass 1374.5. found m/z: [M+H]$^+$= 1375.9, [M+2H]$^{2+}$=688.8.

DTPA-Lys(FI)-Cys(MAL$^a$), (2 in FIG. 8): A solution of 1,4-bis(maleimido)butane (BMB, 3.5 mg, 14 μmol, 3 equiv.) in 700 μL anhydrous DMSO was added to a solution of DTPA-Lys(FI)-Cys-NH$_2$ (5.1 mg, 4.6 μmol) in 230 μL anhydrous DMSO containing DIPEA (1 μL, 5.7 μmol, 1.2 equiv.).

The reaction mixture was stirred overnight at room temperature and purified by RP-HPLC. The fraction was lyophilized. DTPA-Lys(FI)-Cys(MAL$^a$) (3.4 mg, 2.5 μmol, 55% yield) was obtained as a yellow powder. Mass spectrum: $C_{62}H_{74}N_{10}O_{22}S$; MW: 1343.4 g·mol$^{-1}$; calc. exact mass 1342.5. found m/z: [M+H]$^+$=1344.2, [M+2H]$^{2+}$=672.8.

Intermediate DTPA-Lys(CYAL-5.5)-Cys-NH$_2$: A solution of CYAL-5.5, succinimidyl ester (20 mg, 25.9 μmol, 0.7 equiv.) in 200 μL anhydrous DMF was added to a solution of DTPA-Lys-Cys-NH$_2$ (23.7 mg, 38 μmol) in 400 μL anhydrous DMF containing DIPEA (39.7 μL, 227.9 μmol, 6 equiv.). A succinimidyl ester of CYAL-5.5 was prepared. The reaction mixture was stirred for 3 hours at room temperature and purified by RP-HPLC. The fraction collected was lyophilized. DTPA-Lys(CYAL-5.5)-Cys(H)—NH$_2$ (10.6 mg, 7.7 μmol, 30% yield) was obtained as a blue powder. Mass spectrum: $C_{65}H_{85}N_9O_{18}S_3$; MW: 1376.6 g·mol$^{-1}$; calc. exact mass 1375.5. found m/z: [M+H]$^+$=1378.1, [M+2H]$^{2+}$=689.2.

DTPA-Lys(CYAL-5.5)-Cys(NHS$^a$), (3 in FIG. 8): A solution of GMBS (3.7 mg, 13.2 μmol, 2.5 equiv.) in 200 μL anhydrous DMSO was added to a solution of (DTPA)-Lys (CYAL-5.5)-Cys(H)—NH$_2$ (7 mg, 5.2 μmol) in 600 μL anhydrous DMSO containing DIPEA (4 μL, 23.0 μmol, 4.4 equiv.). The reaction mixture was stirred for 5 hours at room temperature and purified by RP-HPLC. The fraction collected was lyophilized. DTPA-Lys(CYAL-5.5)-Cys(NHS$^a$) (5.1 mg, 3.08 μmol, 59% yield) was obtained as a blue powder. Mass spectrum: $C_{77}H_{97}N_{11}O_{24}S_3$; MW: 1656.9 g·mol$^{-1}$; calc. exact mass 1655.6. found m/z: [M+H]$^+$=1657.7 [M+2H]$^+$=829.2.

DTPA-Lys(CYAL-5.5)-Cys(MAL$^a$), (4 in FIG. 8): A solution of BMB (7.8 mg, 31.4 μmol, 12 equiv.) in 400 μL anhydrous DMSO was added to a solution of DTPA-Lys(CYAL-5.5)-Cys(H)—NH$_2$ (3.5 mg, 2.6 μmol) in 300 μL anhydrous DMSO containing DIPEA (2 μL, 11.5 μmol, 4.4 equiv.). The reaction mixture was stirred for 6 hours at room temperature and purified by RP-HPLC. The fraction collected was lyophilized. DTPA-Lys(CYAL-5.5)-Cys(MAL$^a$) (3.1 mg, 1.9 μmol, 73% yield) was obtained as a blue powder. Mass spectrum: $C_{77}H_{97}N_{11}O_{21}S_3$; MW: 1624.9 g·mol$^{-1}$; calc. exact mass 1623.6. found m/z: [M+H]$^+$=1626.1, [M+2H]$^{2+}$=813.3.

Intermediate DOTA-Lys-Cys-Nh$_2$: DOTA-Lys-Cys-NH$_2$ was prepared using SPPS procedures noted earlier. (See Garanger et al., Chem. Commun. 2008 (39) 4792-4) Mass spectrum: $C_{25}H_{46}N_8O_9S$; MW: 634.8 g·mol$^{-1}$; calc. exact mass: 634.3. found m/z: [M+H]$^+$=635.6.

Intermediate DOTA-Lys(NBD)-Cys-NH$_2$: Succinimidyl 6-(N-(7-nitrobenz-2-oxa-1,3-diazol-4-yl)amino)hexanoate (25 mg, 63.9 μmol, 1.1 equiv.) in 500 μL anhydrous DMSO was added to a solution of DOTA-Lys(H)-Cys(H)—NH$_2$ (35.7 mg, 56.2 μmol) in 500 μL anhydrous DMSO. DIPEA (18 μL, 103.3 μmol, 1.8 equiv.) was added and the reaction mixture was stirred for 12 hours at room temperature. After semi-preparative RP-HPLC purification, the fraction collected was lyophilized. DOTA-Lys(NBD)-Cys(H)—NH$_2$ (13.6 mg, 14.9 μmol, 26.6% yield) was obtained as an orange powder. Mass spectrum: $C_{37}H_{58}N_{12}O_{13}S$; MW: 911.0 g·mol$^{-1}$; calculated exact mass: 910.4. found m/z: [M+H]$^+$=911.6.

DOTA-Lys(NBD)-Cys(NHS$^a$), (5 in FIG. 8): A solution of GMBS (10.5 mg, 37.5 μmol, 2.5 equiv.) in 375 μL anhydrous DMSO was added to a solution of DOTA-Lys(NBD)-Cys (H)—NH$_2$ (13.6 mg, 14.9 μmol) in 200 μL anhydrous DMSO containing DIPEA (3 μL, 17.2 μmol, 1.2 equiv.). The reaction mixture was stirred for 12 hours at room temperature. After semi-preparative RP-HPLC purification, the fraction collected was lyophilized. DOTA-Lys(NBD)-Cys(NHS$^a$)—NH$_2$ (12.3 mg, 10.3 μmol, 69.3% yield) was obtained as an orange powder. Mass spectrum: $C_{49}H_{70}N_{14}O_{19}S$; MW: 1191.2 g·mol$^{-1}$; calculated exact mass 1190.5. found m/z: [M+H]$^+$=1191.9.

Intermediate DOTA-Lys(NIR664)-Cys-NH$_2$: A solution of NIR-664-N-succinimidyl ester from Sigma Aldrich (25.0 mg, 34.5 μmol, 0.6 equiv.) in 500 μL anhydrous DMSO was added to DOTA-Lys-Cys-NH$_2$ (33.9 mg, 53.4 μmol). DIPEA (18 μL, 103.3 μmol, 1.9 equiv.) was added and the reaction mixture was stirred overnight at room temperature. After Semi-preparative RP-HPLC purification, the fraction collected was lyophilized. DOTA-Lys(NIR-664)-Cys-NH$_2$ (11.7 mg, 9.4 μmol, 27% yield) was obtained as a blue powder. Mass spectrum: $C_{62}H_{86}N_{10}O_{13}S_2$; MW: 1243.5 g·mol$^{-1}$; calc. exact mass 1242.6. found m/z: [M+H]$^+$=1243.9, [M+2H]$^{2+}$=622.7.

DOTA-Lys(NIR664)-Cys(NHS$^a$), (6 in FIG. 8): A solution of GMBS (5.7 mg, 20.4 μmol, 2.2 equiv.) in 200 μL anhydrous DMSO was added to a solution of DOTA-Lys(NIR-664)-Cys-NH$_2$ (11.7 mg, 9.4 μmol) in 200 μL anhydrous DMSO containing DIPEA (3 μL, 17.2 μmol, 1.8 equiv.). The reaction mixture was stirred overnight at room temperature. After Semi-preparative RP-HPLC purification, the fraction collected was lyophilized. DOTA-Lys(NIR-664)-Cys(NHS$^a$)—NH$_2$ (12.3 mg, 8.1 μmol, 86% yield) was obtained as a blue powder. Mass spectrum: $C_{74}H_{98}N_{12}O_{19}S_2$; MW: 1523.8; calc. exact mass 1522.7. found m/z: [M+H]$^+$=1524.7; [M+2H]$^{2+}$=762.7.

DTPA-Lys(FITC)-Lys(Alkyne)-βAla-Cys(NHS$^a$), (7 in FIG. 10): The linear (DTPA)-Lys(FITC)-Lys-βAla-Cys-NH$_2$ peptide was synthesized as described in Garanger et al., (2008) Simplified syntheses of complex multifunctional nanomaterials. Chem Commun (Camb), 4792-4. A solution of 4-pentynoic acid N-succinimidyl ester (48.8 mg; 250 μmol; 10 equiv.) in 500 μL anhydrous DMSO was added to 250 μL of a solution of DTPA-Lys(FITC)-Lys-βAla-Cys-NH$_2$ (31.0 mg; 25.6 μmol) in anhydrous DMSO containing DIEA (4.5 μL; 25.8 μmol; 1.0 equiv.). The reaction mixture was stirred for 48 hours at room temperature. The reaction mixture was purified by RP-HPLC and the fraction collected lyophilized. DTPA-Lys(FITC)-Lys(Alkyne)-βAla-Cys (11.2 mg, 8.7 μmol, 34% yield) was obtained as a yellow powder. ($C_{58}H_{73}N_{11}O_{19}S_2$) Calc. exact mass: 1291.5. found m/z: [M+H]$^+$=1292.9, [M+2H]$^{2+}$=647.2. DTPA-Lys(FITC)-Lys (Alkyne)-βAla-Cys (11.2 mg; 8.7 μmol) was added to 264 μL of a solution of N-[g-maleimidobutyryloxy]succinimidyl ester (GMBS) (7.4 mg; 26.4 μmol; 3 equiv.). DIEA (1.5 μL; 8.6 μmol; 1 equiv.) was added. The reaction mixture was stirred for 48 hours at room temperature. The reaction mixture was purified by RP-HPLC and the fraction collected lyophilized. DTPA-Lys(FITC)-Lys(Alkyne)-βAla-Cys (NHS) (9.8 mg, 6.2 μmol, 71% yield) was obtained as a yellow powder. ($C_{70}H_{85}N_{13}O_{25}S_2$) MW: 1572.6; Calc. exact mass: 1571.5. found m/z: [M+2H]$^{2+}$=787.3.

DTPA-Lys(FITC)-Lys(PEG$_8$)-βAla-Cys, (8 in FIG. 10): A solution of PEG$_8$-NHS ester (75 μmol; 3.9 equiv.) in 300 μL anhydrous DMSO was added to DTPA-Lys(FITC)-Lys(H)-βAla-Cys(H)—NH$_2$ (23.4 mg; 19.3 μmol). After addition of DIPEA (3.4 μL; 1 equiv.), the reaction mixture was stirred for 48 hours at room temperature. The reaction mixture was purified by semi-preparative RP-HPLC and the fraction collected lyophilized. DTPA-Lys(FITC)-Lys(PEG$_8$)-βAla-Cys (3.6 mg, 2.24 μmol, 11.6% yield) was obtained as a yellow powder. ($C_{71}H_{103}N_{11}O_{27}S_2$) MW: 1606.8; Calc. exact mass: 1605.7. found m/z: [M+H]$^+$=1607.8, [M+2H]$^{2+}$=804.4, [M+3H]$^{3+}$=536.6

DTPA-Lys(FITC)-Lys(PEG$_8$)-βAla-Cys(NHS$^a$), (9 in FIG. 10): GMBS was added to a solution of DTPA-Lys (FITC)-Lys(PEG$_8$)-βAla-Cys(H)—NH$_2$ (3.6 mg; 2.24 μmol) in 404 anhydrous DMSO containing DIPEA. The reaction mixture was stirred for 24 hours at room temperature. The reaction mixture was purified by semi-preparative RP-HPLC and the fraction collected lyophilized. DTPA-Lys(FITC)-Lys (PEG$_8$)-βAla-Cys(NHS$^a$) was obtained as a yellow powder. (C$_{83}$H$_{115}$N$_{13}$O$_{33}$S$_2$) MW: 1887.0; Calc. exact mass: 1885.7. found m/z: [M+H]$^+$=1888.1, [M+2H]$^{2+}$=944.5, [M+3H]$^{3+}$=630.0.

Figure 10:
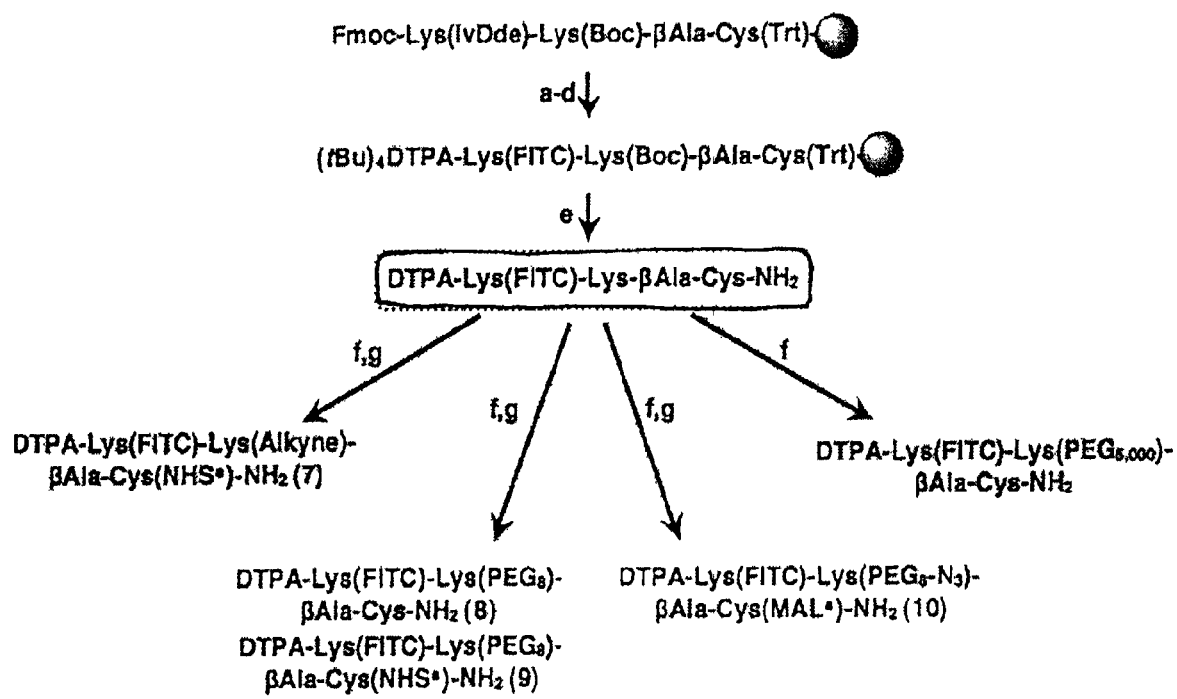
FIG. 10 shows a divergent synthetic strategy for synthesizing trifunctional MSAP's. After cleavage, the DTPA-Lys (FL)-βAla-Cys-$NH_2$ peptide (a common intermediate, gray highlight) was used to make five MSAP's. Here $F^1$=DTPA, $F^2$=FL, see FIG. 7B). Different PEG's ($F^3$, FIG. 7B) and different reactive groups were attached. MSAP functional groups can provide multimodal detection (DTPA, FL), modify substrate properties ($PEG_{5000}$, $PEG_8$), or equip a probe with groups for subsequent reactions using click chemistry. Reaction conditions: Fmoc/tBu SPPS: a) Piperidine/DMF; b) $(tBu)_4$DTPA, PyBOP, DIPEA, DMF; c) Hydrazine/DMF; d) FL, DIPEA, DMF; e) TFA/TIS/$H_2$O/EDT; f) $F^3$-NHS, DIPEA, DMSO/DMF; g) Cross-linking agent (GMBS or BMB), DIPEA, DMSO/DMF.

DTPA-Lys(FITC)-Lys(PEG$_8$-N$_3$)-βAla-Cys(MAL$^a$), 10 in FIG. 10): DTPA-Lys(FITC)-Lys(H)-βAla-Cys(H)—NH$_2$ (27.2 mg; 22.4 μmol) was added to 3.3 mL of a solution of 1,4-bismaleimidobutane (16.3 mg; 39.8 μmol; 3.0 equiv.) containing DIEA (5 μL; 28.7 μmol; 1.3 equiv.). The reaction mixture was stirred for 24 hours at room temperature. A solution of azido-dPEG$_8$-NHS ester (42.9 mg; 75 μmol; 3.3 equiv.) in 300 μL anhydrous DMSO was added. The reaction mixture was stirred for another 46 hours at room temperature. The reaction mixture was purified by RP-HPLC and the fraction collected lyophilized. DTPA-Lys(FITC)-Lys(PEG$_8$-Azido)-βAla-Cys(Maleimide) (8.6 mg, 4.5 μmol, 20% yield) was obtained as a yellow powder. (C$_{84}$H$_{118}$N$_{18}$O$_{31}$S$_2$) MW: 1910.0; Calc. exact mass: 1908.7. found m/z: [M+H]$^+$=1910.3, [M+2H]$^{2+}$=955.8.

MSAP-annexin V Synthesis: To 100 μL of annexin V (0.354 mg, 9.83 nmoles) in 0.05M NaHCO$_3$ buffer, pH 8.1 was added 5.5 μL of 3 (55 nmoles) in DMSO. After 15 minutes at room temperature in the dark, the mixture was applied to a PD-10 column in PBS. The high molecular weight fraction was collected. The number of MSAP's per annexin (0.7) was determined from absorbances at 280 nm (annexin V) and 682 nm (NIR664 fluorochrome). APC-annexin V was from InVitrogen. Cells were stained and analyzed by flow cytometric analysis (FACS) as described in Smith et al., (2009) The antiproliferative cytostatic effects of a self-activating viridin prodrug. *Mol Cancer Ther* 8, 1666-75.

Results

Figure 8:
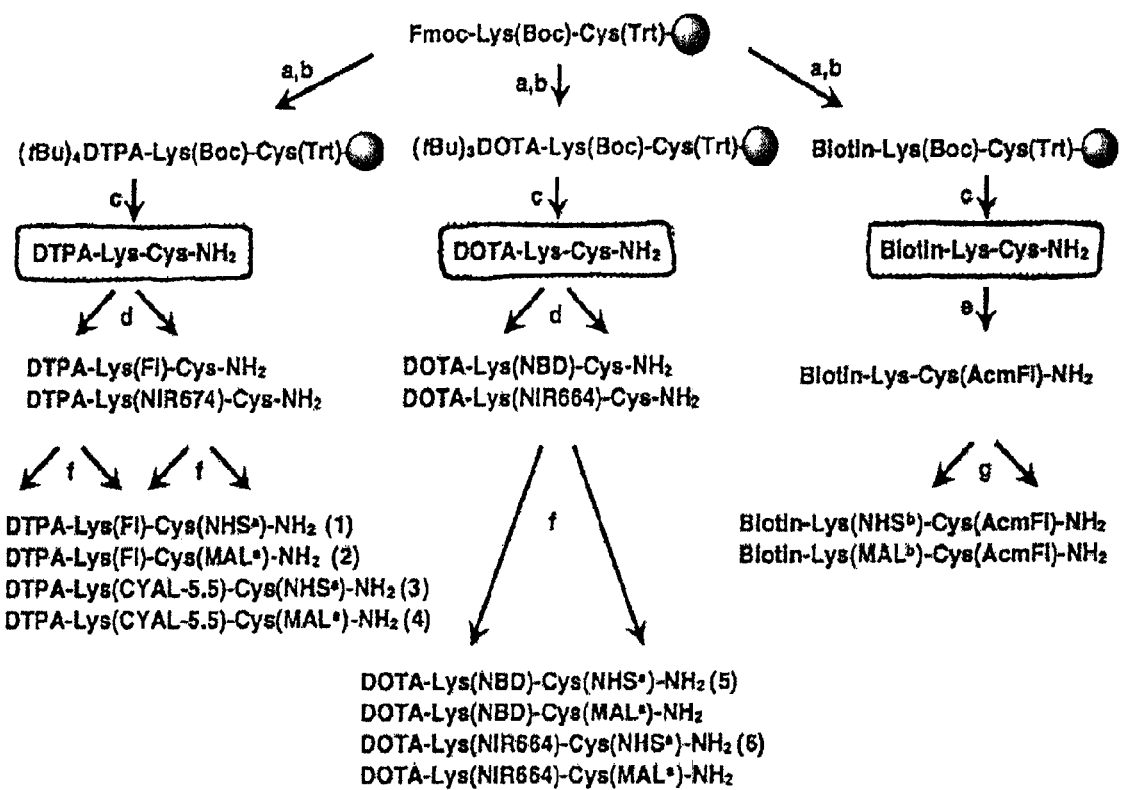
FIG. 8 shows a divergent synthetic strategy for synthesizing fluorochrome-chelate MSAP's. The chelators (DOTA or DTPA, the $F^1$ group in FIG. 7B) were attached on the solid phase. After cleavage, these $F^1$-Lys-Cys-$NH_2$ peptides (gray highlights) served as common intermediates and were split to make a total of 8 fluorochrome-chelator MSAPs. Fluorochromes ($F^2$, FIG. 7B) were 6-(fluorescein-5-carboxyamido) hexanoyl (FI), NIR674, NBD or NIR664. The reactive groups (RG, FIG. 7B) were an NHS ester (NHS) or a maleimide (MAL). Two additional fluorochrome-biotin MSAPs using the same peptide scaffold are also shown and are from Garanger, et al., (2009) A multifunctional single-attachmentpoint reagent for controlled protein biotinylation. *Bioconjug Chem* 20, 170-3. Reaction conditions: Fmoc/tBu SPPS: a) Piperidine/DMF; b) (tBu-Protected)$F^1$, PyBOP, DIPEA, DMF; c) TFA/TIS/$H_2$O/EDT; d) $F^2$-NHS, DIPEA, DMSO/DMF; e) Fluorescein-5-iodoacetamide, DIPEA, DMF; f) Cross-linking agent (GMBS or BMB), DIPEA, DMSO/DMF; g) Cross-linking agent (DSS or GMBS), DIPEA, DMSO/DMF).
Figure 9:
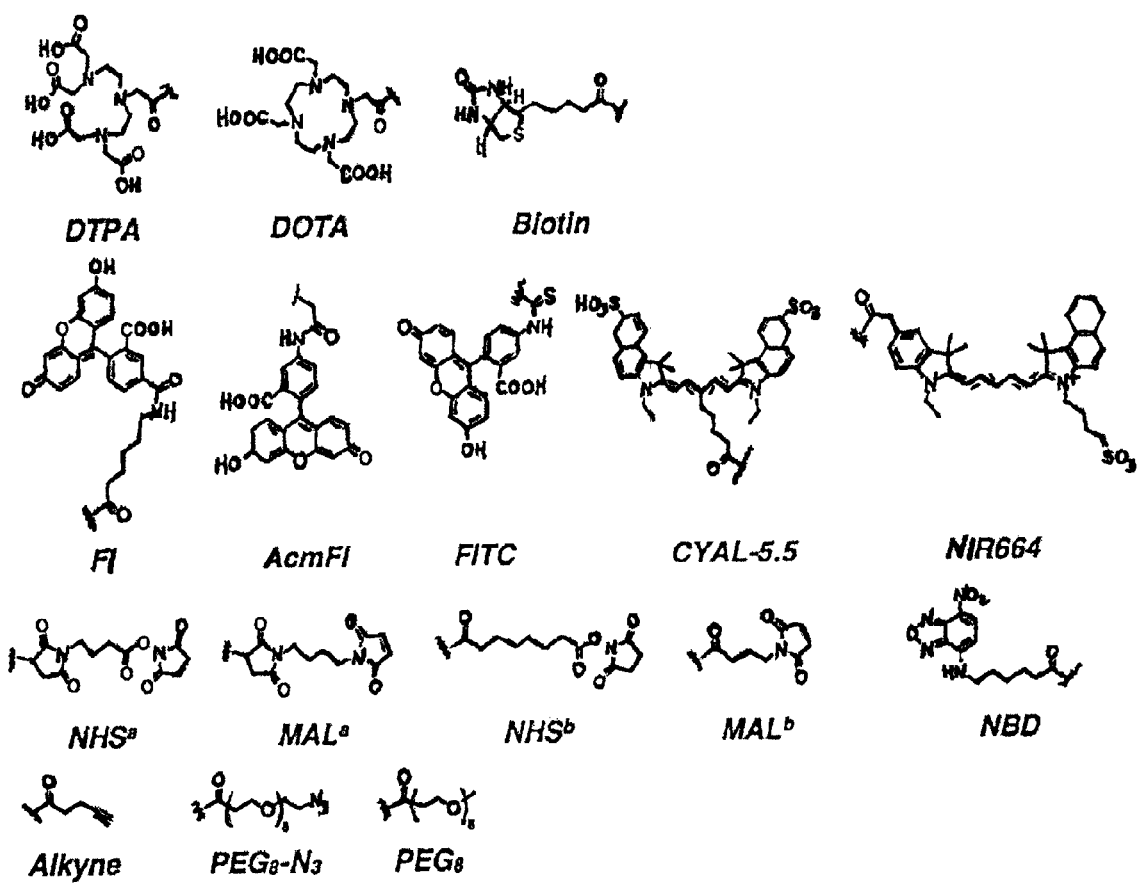
FIG. 9 shows non-limiting examples of functional groups used in MSAP reagents.

The use of a divergent strategy using a dipeptide scaffold to obtain bifunctional MSAP fluorochrome-chelates is shown in FIG. 8. The Fmoc-Lys(Boc)-Cys(Trt) peptide was made manually, on a scale sufficient to support the number of individual MSAP reagents to eventually be synthesized (about 0.2 mmoles peptide). Removal of the N-terminal Fmoc protecting group then allowed a functional group to be attached to the N-terminus. For fluorochrome-chelator MSAP's, we attached DTPA or DOTA to the N-terminus, followed by cleavage and storage of the DTPA-Lys-Cys or DOTA-Lys-Cys dipeptides. The cleaved dipeptides then featured a single primary amine, which was used for the attachment of one of four fluorochromes (NBD, fluorescein, NIR664, CYAL-5.5 (also called NIR674)). Finally, a commercially available bifunctional reagent was used to attach a reactive group (RG) to the thiol of cysteine, yielding a total of 8 maleimide (MAL) or an NHS ester (NHS) MSAP reagents. Structures of functional groups and reactive groups are shown in FIG. 9. The "a" or "b" designation in MAL$^a$ or NHS$^a$ of FIG. 8 refers to the use of slightly different linkers between the cysteine thiol and MAL or NHS reactive groups. The syntheses of compounds I-6 of FIG. 8 are provided in the Experimental Methods of Example 5 above. In another demonstration of a divergent synthetic strategy starting point of these syntheses, the Fmoc-Lys(Boc)-Cys(Trt) peptide, was used to obtain fluorochrome-biotins (see Garanger et al., (2009) A multifunctional single-attachment-point reagent for controlled protein biotinylation. *Bioconjug Chem* 20, 170-3).

An advantage of the MSAP strategy for obtaining fluorochrome-chelates is that additional functional groups beyond the fluorochrome and chelate can be added by using the Fmoc-Lys(ivDde)-Lys(Boc)-βAla-Cys(Trt) tetrapeptide as scaffold (see FIG. 10). After synthesizing the peptide, DTPA and fluorescein were added to the N-terminus and the epsilon amino group of N-terminal lysine, respectively. Cleavage and deprotection yielded fluorochrome-chelate tetrapeptides that featured a single amino group and a single thiol reactive group, enabling two additional chemoselective reactions to be performed in solution. For example, the amino group was used to attach PEG$_8$ (MW=400 Da) or PEG$_{5000}$ (MW=5000 Da), modifying the molecular and hydrophilicity of the substrate, while it can be detected by fluorescence or from the presence of a radioactive metal. The syntheses of compounds 7-10 of FIG. 10 are provided in the Experimental Methods of Example 5 above.

Summaries of MSAPs made in FIGS. 8 and 10 are provided in Tables 4 and 5. Functional groups for both Tables are given in FIG. 9.

TABLE 4

Summary of Bifunctional MSAPs Based On the Lys-Cys-NH$_2$ Peptide Scaffold

| Designation | Scaffold | F$^1$ | F$^2$ | Reactive Group (RG) |
|---|---|---|---|---|
| DTPA-Lys(NBD)-Cys(NHS$^a$)* | | DTPA | NBD | NHS$^a$ |
| DTPA-Lys(FI)-Cys(NHS$^a$), Cmpd (1) | | DTPA | FI | NHS$^a$ |
| DTPA-Lys(FI)-Cys(MAL$^a$) (2) | | DTPA | FI | MAL$^a$ |
| DTPA-Lys(CYAL-5.5)-Cys(NHS$^a$) (3) | | DTPA | CYAL-5.5 | NHS$^a$ |
| DTPA-Lys(CYAL-5.5)-Cys(MAL$^a$) (4) | | DTPA | CYAL-5.5 | MAL$^a$ |
| DOTA-Lys(NBD)-Cys(NHS$^a$) (5) | | DOTA | NBD | NHS$^a$ |
| DOTA-Lys(NBD)-Cys(MAL$^a$) | | DOTA | NBD | MAL$^a$ |
| DOTA-Lys(NIR664)-Cys(NHS$^a$) (6) | | DOTA | NIR664 | NHS$^a$ |
| DOTA-Lys(NIR664)-Cys(MAL$^a$) | | DOTA | NIR664 | MAL$^a$ |

TABLE 4-continued

Summary of Bifunctional MSAPs Based On the Lys-Cys-$NH_2$ Peptide Scaffold

| Designation | Scaffold | $F^1$ | $F^2$ | Reactive Group (RG) |
|---|---|---|---|---|
| Biotin-Lys($NHS^b$)-Cys(AcmFl)** | | Biotin | AcmFl | $NHS^b$ |
| Biotin-Lys($MAL^b$)-Cys(AcmFl), | | Biotin | AcmFl | $MAL^b$ |

*Garanger et al., (2008) Simplified syntheses of complex multifunctional nanomaterials. *Chem Commun* (Camb), 4792-4.
**Garanger, et al., (2009) A multifunctional single-attachment-point reagent for controlled protein biotinylation. *Bioconjug Chem* 20, 170-3.

TABLE 5

Summary of trifunctional MSAPs Based on the Lys-Cys-βAla-Cys-$NH_2$ Peptide Scaffold

| Designation | Scaffold | $F^1$ | $F^2$ | $F^3$ | Reactive Group |
|---|---|---|---|---|---|
| DTPA-Lys(FITC)-Lys($PEG_{5,000}$)-βAla-Cys,* | | DTPA | FITC | $PEG_{5,000}$ | Thiol |
| DTPA-Lys(FITC)-Lys(Alkyne)-βAla-Cys($NHS^a$), cmpd (7) | | DTPA | FITC | Alkyne | $NHS^a$ |
| DTPA-Lys(FITC)-Lys($PEG_8$)-βAla-Cys (8) | | DTPA | FITC | $PEG_8$ | Thiol |
| DTPA-Lys(FITC)-Lys($PEG_8$)-βAla-Cys($NHS^a$) (9) | | DTPA | FITC | $PEG_8$ | $NHS^a$ |
| DTPA-Lys(FITC)-Lys($PEG_8$-$N_3$)βAla-Cys($MAL^a$) (10) | | DTPA | FITC | $PEG_8$-Azido | $MAL^a$ |

*Garanger et al., (2008) Simplified syntheses of complex multifunctional nanomaterials. *Chem Commun* (Camb), 4792-4.

Figure 11:
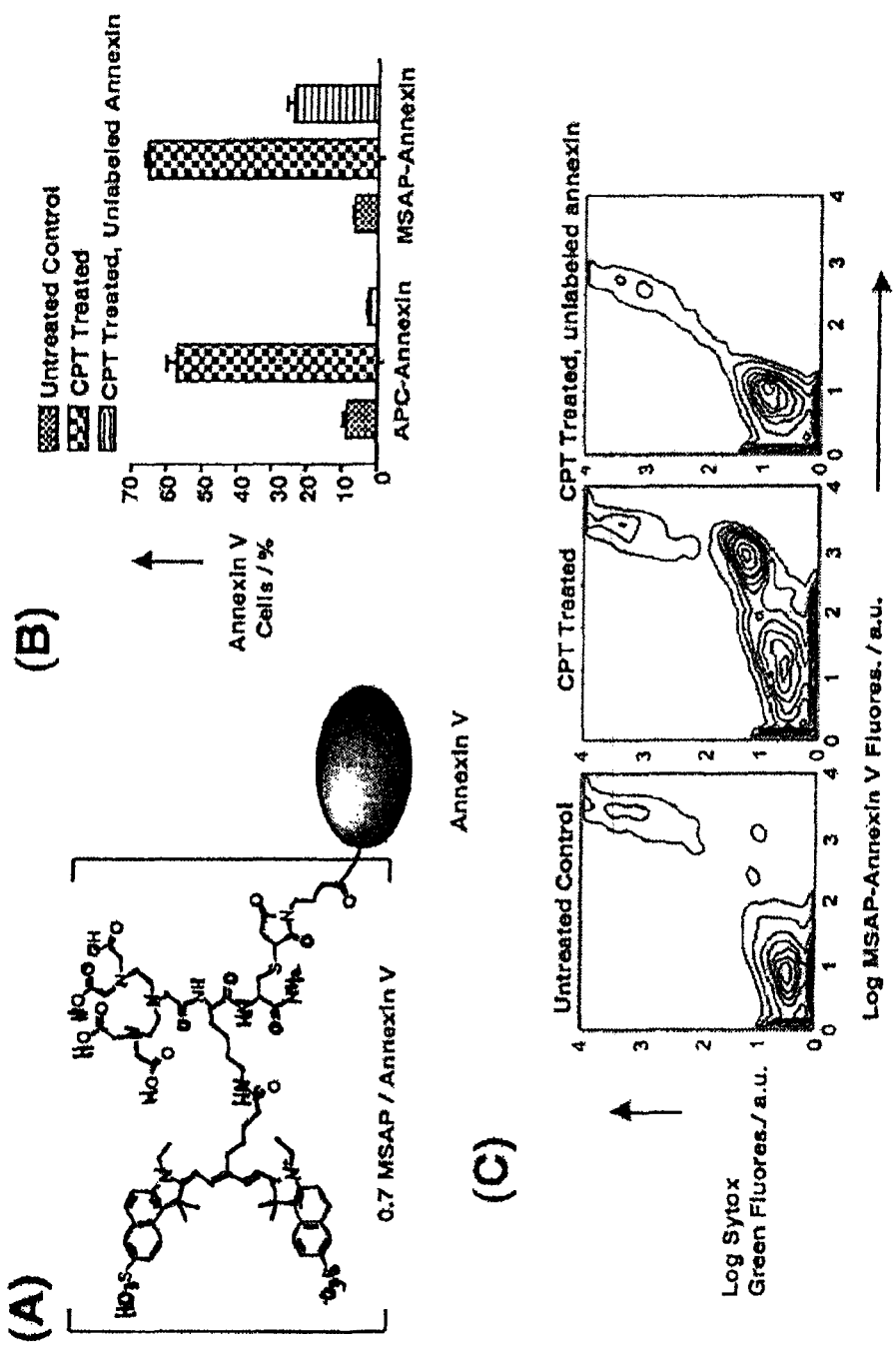
FIG. 11 shows detection of apoptotic and necrotic cells using a multifunctional MSAP-annexin V by dual wavelength FACS. In (A), there is a schematic depiction of the MSAP-annexin V probe. Compound 3 was reacted with annexin V to obtain an annexin V modified with 0.7 MSAP per mole of protein (0.7 fluorochrome, 0.7 DTPA). In (B), MSAP-annexin V was bound to apoptotic or necrotic A549 cells. In (C), MSAP-annexin V was bound to apoptotic Jurkat T cells. Apoptosis (right, bottom quadrant) was induced by 5 μM camptothecin (CPT) in (B) and (C).
Figure 12:
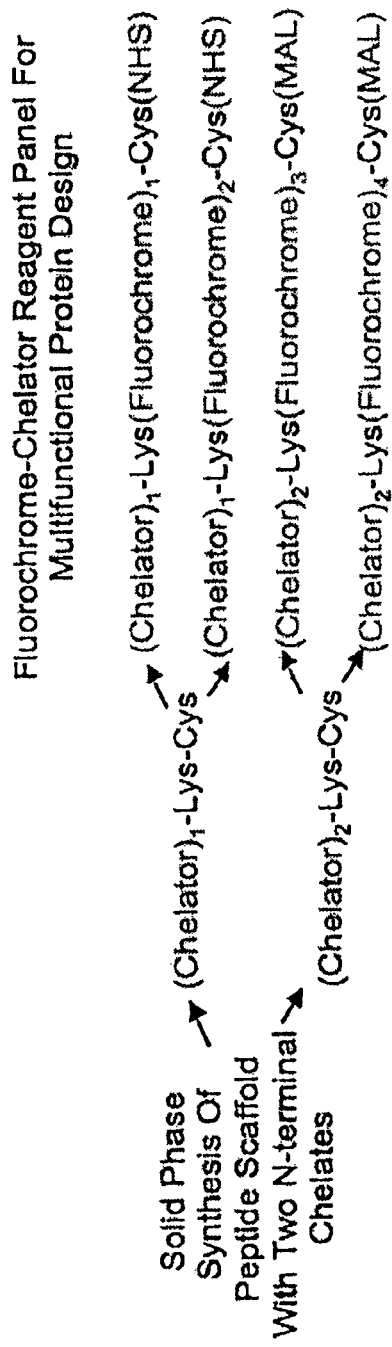
FIG. 12 shows how the invention provides a divergent synthetic strategy using a peptide scaffold leads to a panel of fluorochrome-chelators with maleimide (MAL) or N-hydroxysuccinimide (NHS) groups for attachment to proteins.

To demonstrate the ability of an MSAP regent to generate a multifunctional protein, we reacted DTPA-Lys(CYAL-5.5)-Cys($NHS^a$) (3 of FIG. 8) with annexin V, to obtain a fluorescent annexin capable of chelating metals and which featured 0.7 MSAP's per mole of protein, (see FIG. 11). Annexin V is a 33 kDa protein which undergoes inactivation with the modification of more than one amino group per mole of protein (see Schellenberger et al. noted above). The MSAP reagent permitted quantitation of the number of DTPA's per annexin through absorbance of the fluorochrome, while the single attachment point feature permitted the attachment of 1.4 moles of functional groups per mole of annexin V (0.7 DTPA plus 0.7 CYAL-5.5) with the modification of only 0.7 amines per mole (see FIG. 11(A)). The MSAP-annexin bound camptothecin treated apoptotic A549 cells (see FIG. 11(B)), with the binding blocked by unlabeled annexin V. Here annexin V binding bound to both apoptotic and necrotic cells, but not healthy cells.

Discussion

In Example 5, we show how MSAP chemistry was employed with a divergent synthetic strategy, where intermediates are stored and then split for reaction with different functional groups, to yield fluorochrome-chelates. Some of fluorochrome-chelates featured as additional functional groups like PEG's or click chemistry reactive groups (e.g., alkyne). While we have employed two chelators (DTPA, DOTA) and four fluorochromes (NBD, fluorescein, NIR664; CYAL-5.5), the peptide scaffold approach permits substitutions. The functional groups attached to peptides on the solid phase must survive the conditions of deprotection. When functional groups were attached to solid phase peptides, the reaction was somewhat less efficient, with respect to the consumption of functional groups, than when the attachment was made with solution phase reactions.

By switching from the Lys-Cys-$NH_2$ dipeptide scaffold to the Lys-Lys-βAla-Cys-$NH_2$ tetrapeptide scaffold, an additional functional group such as PEG's or click chemistry reactive groups were attached to MSAP reagents along with the fluorochromes and chelating groups.

A common problem when attempting to obtain multifunctional versions of small proteins is the small of number of amino acid residues available for modification with retention of full bioactivity. To illustrate the ability of MSAP's to address this problem, a fluorochrome-chelate MSAP was reacted with annexin V to obtain an MSAP-annexin V which features a total 1.4 moles of functional groups per mole of protein with the single attachment point features of the MSAP reagent only 0.7 moles of modified lysine. Annexin V is progressively inactivated by the reaction of more than one amino group per mole (see Schellenberger et al. noted above). The problem arises not only with small proteins like annexin V, where the random reaction of amines with N-hydroxysuccinimide (NHS) esters produces inactivation, but also with many rDNA engineered proteins which are designed with a single reactive thiol to accommodate modification (see, Li et al., (2008) Site-specific labeling of annexin V with F-18 for apoptosis imaging. *Bioconjug Chem* 19, 1684-8).

Another benefit of MSAP fluorochrome-chelates is the ready determination of the numbers of chelating groups on chelator-proteins. Here we employed the absorbance of NIR664 to determine the number of DTPA's attached per mole of annexin V. For low numbers of chelate per protein, fluorescence can be employed, as we shown with a fluorochrome-biotin-cetuximab compounds (see, Garanger et al., (2009) A multifunctional single-attachment-point reagent for controlled protein biotinylation. Bioconjug Chem 20, 170-3).

In conclusion, multifunctional single attachment point reagents were synthesized using efficient divergent strategies as detailed in Example 5 and shown in FIGS. 7-11, yielding a variety of fluorochrome-chelates for the modification of proteins. MSAP reagents offer new possibilities for the design of multifunctional proteins employing protein substrates that are easily inactivated by conversion of their epsilon amines to amides or which contain a single thiol for modification.

Thus, Example 5 provides two examples of two divergent synthetic strategies for the design of multifunctional single attachment point (MSAP) reagents which feature reactive groups that enable them to be conjugated to protein substrates. Acid insensitive chelators or fluorochromes were attached to Lys-Cys-NH2 or Lys-Lys-βAla-Cys-NH$_2$ peptide scaffolds. After cleavage from their supports, the modified peptides were split; that is they were then further modified by separate solution phase reactions by the attachment of other functional groups and a reactive groups such as maleimides or NHS esters. A variety of fluorochrome-chelates for protein modification were obtained, with some possessing additional functional groups like PEG polymers of click chemistry reactive alkynes and azides. A fluorochrome-chelate MSAP reagent was reacted with annexin V, to obtain a protein functionalized with 0.7 moles the chelator and 0.7 moles of fluorochrome per mole of annexin. Though the MSAP-annexin contains a total 1.4 moles of functional groups per mole of protein, and 1.4 moles of amine modification inactivates annexin V, the MSAP-annexin V maintained full bioactivity because of the single attachment used by the MSAP reagent. The divergent synthetic strategy allowed a variety of MSAP reagents to be efficiently generated, which can be used to obtain multifunctional proteins like annexin V.

Therefore, the invention provides multifunctional probes that can be synthesized in a single step using peptide scaffold-based multifunctional single-attachment-point reagents. To obtain multifunctional probes using the methods of the invention, a substrate is reacted with a multifunctional single-attachment-point (MSAP) reagent. The MSAP reagents can include three components: (i) a peptide scaffold, (ii) a single chemically reactive group for reaction of the MSAP with a substrate having a complementary reactive group, and (iii) multiple functional groups.

Although the present invention has been described in detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A method for preparing a multifunctional probe, the method comprising:
   (a) attaching at least one functional group capable of surviving deprotection to a peptide scaffold in a solid phase;
   (b) cleaving the peptide scaffold from the solid phase into a solution phase under deprotection conditions;
   (c) attaching at least one additional functional group to the peptide scaffold in the solution phase under non-deprotection conditions to create a reagent having at least two attached functional groups and a reactive group, wherein the reactive group is either part of the peptide scaffold of step (a) or is attached to the peptide scaffold in a separate step; and
   (d) attaching the reagent to a substrate by reaction of the reactive group with a complementary reactive group of the substrate.

2. The method of claim 1 wherein:
   the reagent is prepared to yield a predetermined stoichiometric ratio of the functional group(s) attached in step (a) and the additional functional group(s) attached in step (c) on the scaffold.

3. The method of claim 1 wherein:
   the substrate is selected from nanoparticles, proteins, enzymes, cyclic peptides, linear peptides, antibodies, drugs and vitamins.

4. The method of claim 1 wherein:
   the reactive group of the scaffold and the complementary reactive group of the substrate is a single attachment point for the scaffold and the substrate.

5. The method of claim 1 wherein:
   at least one of the functional group(s) attached in step (a) and the additional functional group(s) attached in step (c) is a chelate.

6. The method of claim 5 wherein:
   the chelate includes a magnetic material.

7. The method of claim 5 wherein:
   the chelate includes a paramagnetic or superparamagnetic material.

8. The method of claim 1 wherein:
   at least one of the functional group(s) attached in step (a) and the additional functional group(s) attached in step (c) includes a positron-emitting radionuclide or a gamma radiation-emitting radionuclide.

9. The method of claim 1 wherein:
   at least one of the functional group(s) attached in step (a) and the additional functional group(s) attached in step (c) is radiopaque.

10. The method of claim 1 wherein:
    at least one of the functional group(s) attached in step (a) and the additional functional group(s) attached in step (c) absorbs photons.

11. The method of claim 1 wherein:
    at least one of the functional group(s) attached in step (a) and the additional functional group(s) attached in step (c) is a fluorochrome.

12. The method of claim 1 wherein:
    at least one of the functional group(s) attached in step (a) and the additional functional group(s) attached in step (c) is selected from proteins, vitamins, enzymes, peptides, antibodies, and drugs that can target a site in a patient.

13. The method of claim 1 wherein:
at least one of the functional group(s) attached in step (a) and the additional functional group(s) attached in step (c) is a polymer.

14. The method of claim 1 wherein:
at least one of the functional group(s) attached in step (a) and the additional functional group(s) attached in step (c) is a hapten.

15. The method of claim 1 wherein:
at least one of the functional group(s) attached in step (a) and the additional functional group(s) attached in step (c) is a charged polymer.

16. The method of claim 1 wherein:
at least one of the functional group(s) attached in step (a) and the additional functional group(s) attached in step (c) is a dispersion stabilizing agent.

17. The method of claim 1 wherein:
the reactive group is selected from the group consisting of N-hydroxysuccinimide ester, maleimide, thiol, alkyne, azide, and aldehyde.

18. The method of claim 1 wherein:
the peptide scaffold includes 20 or less amino acid residues.

19. The method of claim 1 wherein:
the functional group attached in step (a) is attached to one amino acid residue of the peptide scaffold and the additional functional group attached in step (c) is attached to another amino acid residue of the peptide scaffold.

20. The method of claim 1 wherein:
the peptide scaffold includes a spacer residue that is not attached to any of the functional groups.

\* \* \* \* \*